(12) United States Patent
Kokish et al.

(10) Patent No.: US 6,485,500 B1
(45) Date of Patent: Nov. 26, 2002

(54) EMBOLI PROTECTION SYSTEM

(75) Inventors: Arkady Kokish, San Jose, CA (US); Daryush Mirzaee, Sunnyvale, CA (US); Eric J. Penn, Morgan Hill, CA (US); Benjamin C. Huter, Murrieta, CA (US); Kent C. B. Stalker, San Marcos, CA (US); Gregg A. Jackson, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/531,740

(22) Filed: Mar. 21, 2000

(51) Int. Cl.$^7$ .................. A61M 29/00; A61M 31/00
(52) U.S. Cl. .............. 606/194; 606/200; 604/101.01; 604/101.03; 604/101.05; 604/103.01; 604/919
(58) Field of Search .............. 604/96.01, 99.02, 604/99.03, 99.04, 101.01, 101.02, 101.03, 101.04, 101.05, 102.01, 102.02, 103.01, 103.02, 103.06, 103.07, 915, 919; 606/192, 194, 200

(56) References Cited

U.S. PATENT DOCUMENTS

| | | | |
|---|---|---|---|
| 3,952,747 A | | 4/1976 | Kimmell, Jr. |
| 4,423,725 A | * | 1/1984 | Baran et al. ............ 128/207.15 |
| 4,425,908 A | | 1/1984 | Simon |
| 4,494,531 A | | 1/1985 | Gianturco |
| 4,612,931 A | | 9/1986 | Dormia |
| 4,619,246 A | | 10/1986 | Molgaard-Nielsen et al. |
| 4,643,184 A | | 2/1987 | Mobin-Uddin |
| 4,650,466 A | | 3/1987 | Luther |
| 4,662,885 A | | 5/1987 | DiPisa, Jr. |
| 4,688,553 A | | 8/1987 | Metals |
| 4,706,671 A | | 11/1987 | Weinrib |
| 4,723,549 A | | 2/1988 | Wholey et al. |
| 4,727,873 A | | 3/1988 | Mobin-Uddin |
| 4,781,177 A | | 11/1988 | Lebigot |
| 4,790,812 A | | 12/1988 | Hawkins, Jr. et al. |

(List continued on next page.)

FOREIGN PATENT DOCUMENTS

| | | |
|---|---|---|
| EP | 0 427 429 A2 | 5/1991 |
| EP | 0 472 334 A1 | 2/1992 |
| EP | 11164890 | 6/1999 |
| WO | WO92/03097 | 3/1992 |
| WO | WO96/01591 | 1/1996 |
| WO | WO97/17100 | 5/1997 |
| WO | WO 99/08744 | 2/1999 |
| WO | WO99/23976 | 5/1999 |
| WO | WO 99/40964 | 8/1999 |

*Primary Examiner*—Edward K. Look
*Assistant Examiner*—Richard A. Edgar
(74) *Attorney, Agent, or Firm*—Fulwider Patton Lee & Utecht, LLP

(57) ABSTRACT

The emboli protection system provides one or more inflatable blocking balloons for isolation of a section of a blood vessel to prevent migration of emboli from the section during an interventional procedure, and fluid infusion and evacuation ports for flushing emboli from the isolated section. One embodiment provides for a distal blocking balloon catheter, over which an interventional device can be introduced, and a proximal blocking balloon catheter to be introduced over the interventional device for isolating a portion of a blood vessel to be treated. The blocking balloons can be perforated to provide the infusion ports, and thrombolytic inflation fluid may be used to break down and dissolve thrombus and plaque in the isolated portion of the blood vessel. The interventional therapeutic device such as an angioplasty balloon catheter may be incorporated into the distal blocking balloon catheter, or the distal and blocking proximal balloon catheters can be incorporated with the interventional therapeutic device together in one device. Infusion ports may also be provided in either or both of the distal and proximal blocking catheters.

39 Claims, 11 Drawing Sheets

U.S. PATENT DOCUMENTS

| | | | |
|---|---|---|---|
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |
| 4,990,156 A | 2/1991 | Lefebvre | |
| 4,997,435 A | 3/1991 | Demeter | |
| 4,998,539 A | 3/1991 | Delsanti | |
| 5,053,008 A | 10/1991 | Bajaj | |
| 5,064,428 A | 11/1991 | Cope et al. | |
| 5,071,407 A | 12/1991 | Termin et al. | |
| 5,092,839 A | 3/1992 | Kipperman | |
| 5,100,425 A | 3/1992 | Fischell et al. | |
| 5,102,415 A | 4/1992 | Guenther et al. | |
| 5,108,419 A | 4/1992 | Reger et al. | |
| 5,135,484 A * | 8/1992 | Wright | 604/101.03 |
| 5,152,777 A | 10/1992 | Goldberg et al. | |
| 5,160,342 A | 11/1992 | Reger et al. | |
| 5,163,906 A * | 11/1992 | Ahmadi | 604/101.03 |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,383,887 A | 1/1995 | Nadal | |
| 5,397,307 A * | 3/1995 | Goodin | 604/101.03 |
| 5,411,479 A * | 5/1995 | Bodden | 604/101.03 |
| 5,421,832 A | 6/1995 | Lefebvre | |
| 5,462,529 A * | 10/1995 | Simpson et al. | 604/101.04 |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,536,252 A * | 7/1996 | Imran et al. | 604/101.02 |
| 5,549,626 A | 8/1996 | Miller et al. | |
| 5,599,307 A * | 2/1997 | Bacher et al. | 604/101.05 |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,662,671 A | 9/1997 | Barbut et al. | |
| 5,669,933 A | 9/1997 | Simon et al. | |
| 5,674,198 A * | 10/1997 | Leone | 604/101.05 |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,728,068 A * | 3/1998 | Leone et al. | 604/101.01 |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maahs | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,925,016 A * | 7/1999 | Chornenky et al. | 604/19 |
| 5,941,896 A | 8/1999 | Kerr | |
| 5,947,985 A * | 9/1999 | Imran | 604/101.05 |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,013,093 A | 1/2000 | Nott et al. | |
| 6,022,336 A * | 2/2000 | Zadno-Azizi et al. | 604/101.05 |
| 6,270,477 B1 * | 8/2001 | Bagaoisan et al. | 604/102.01 |

* cited by examiner

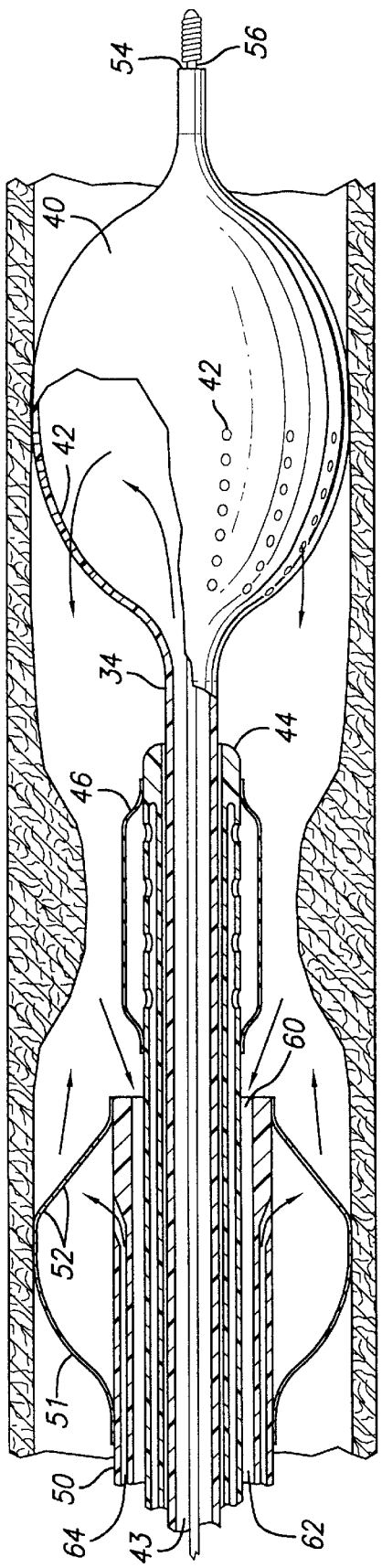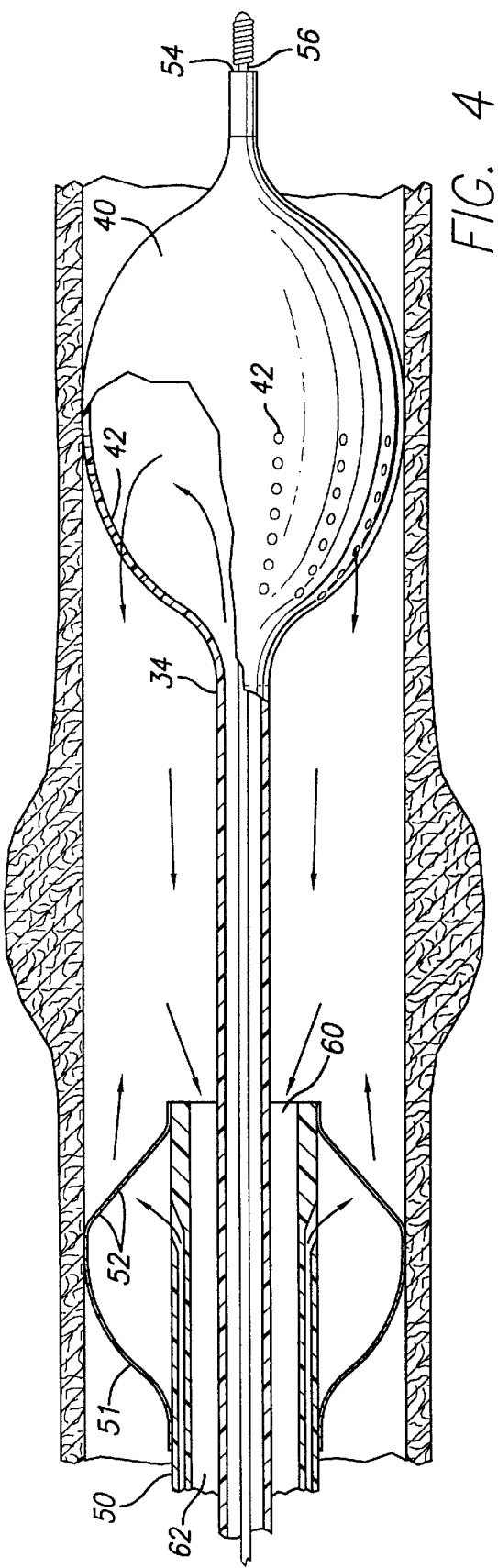

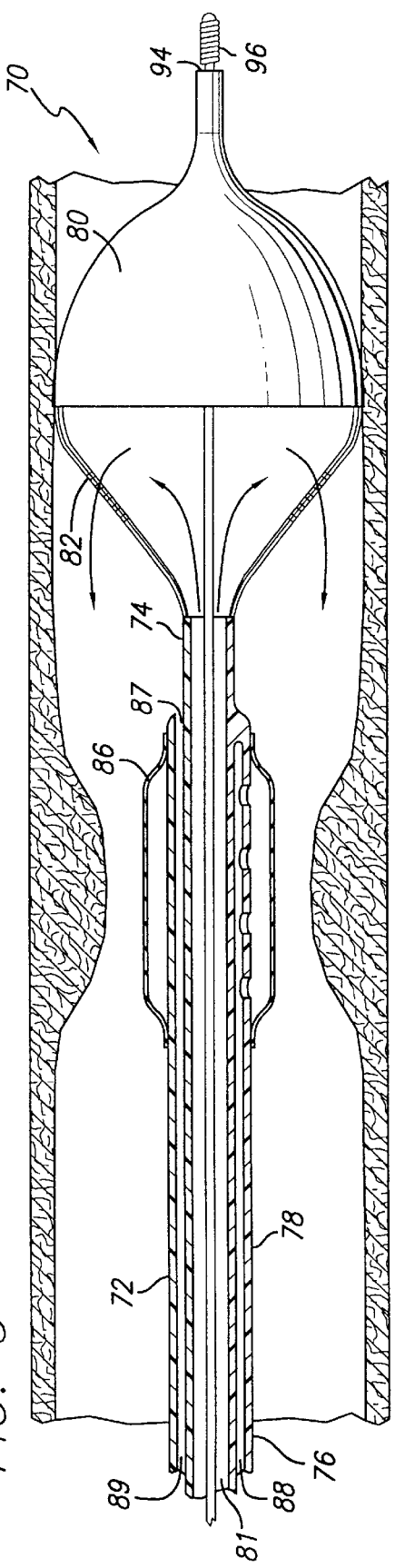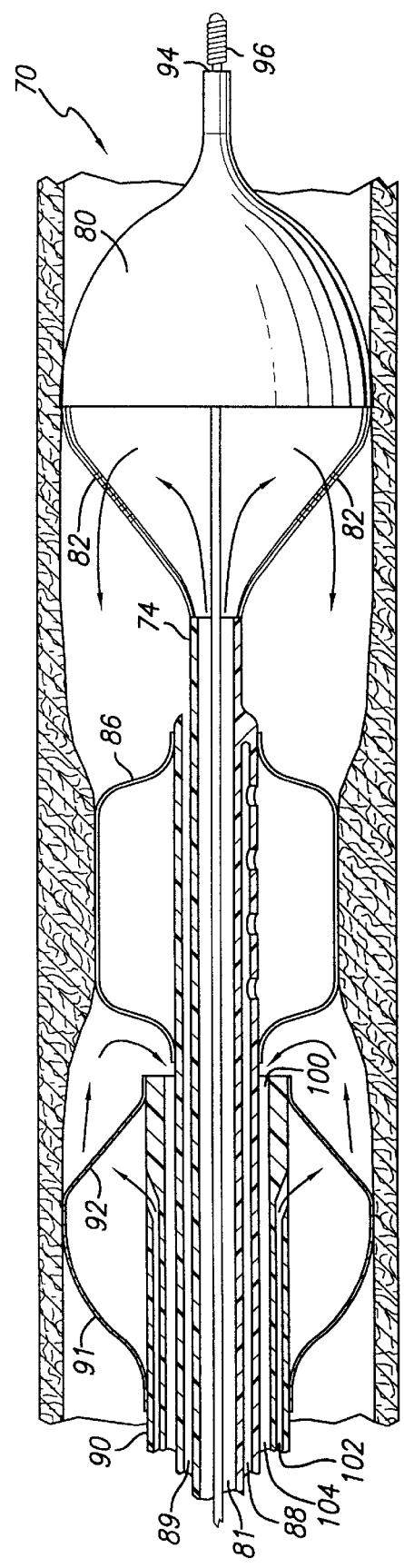

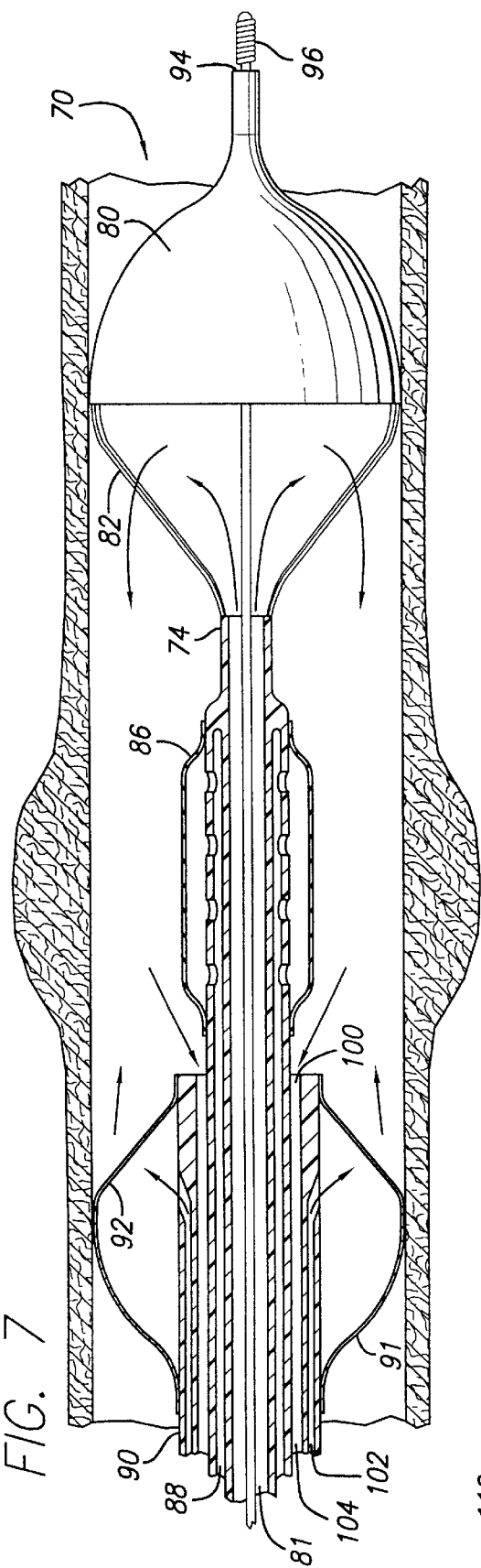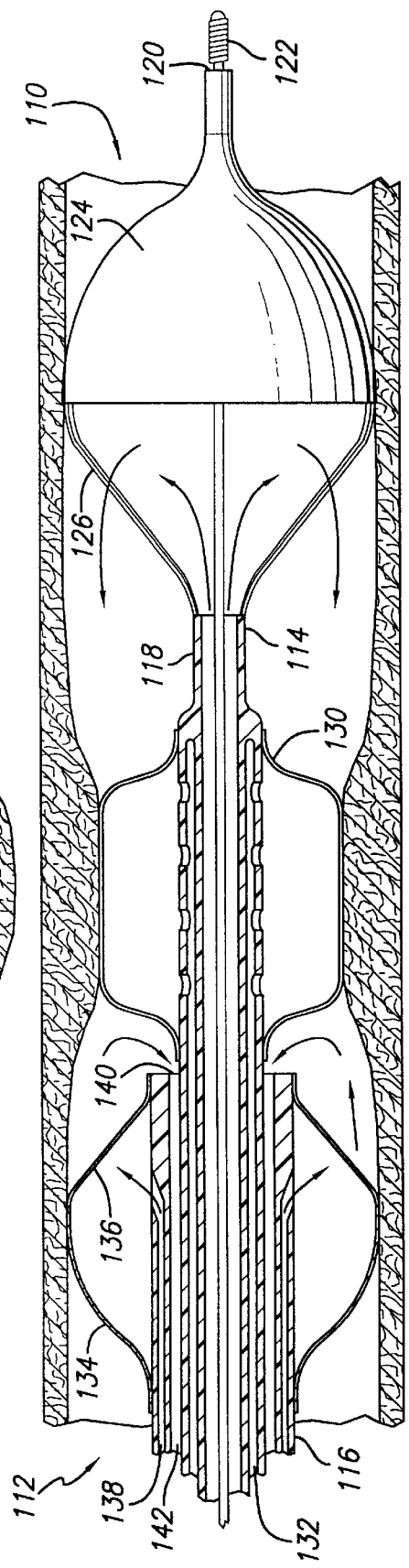

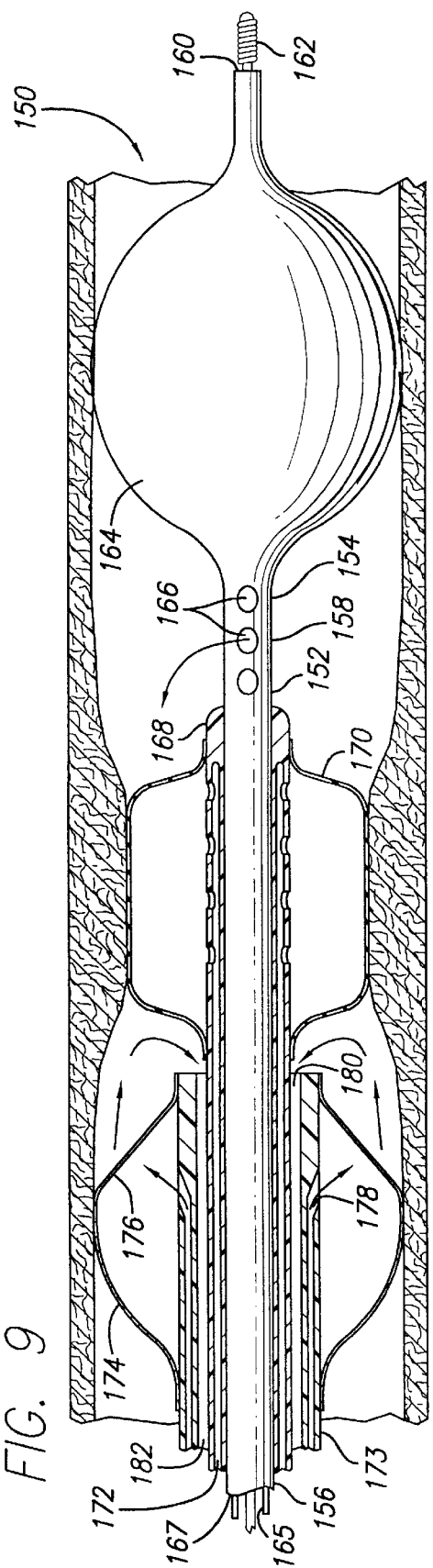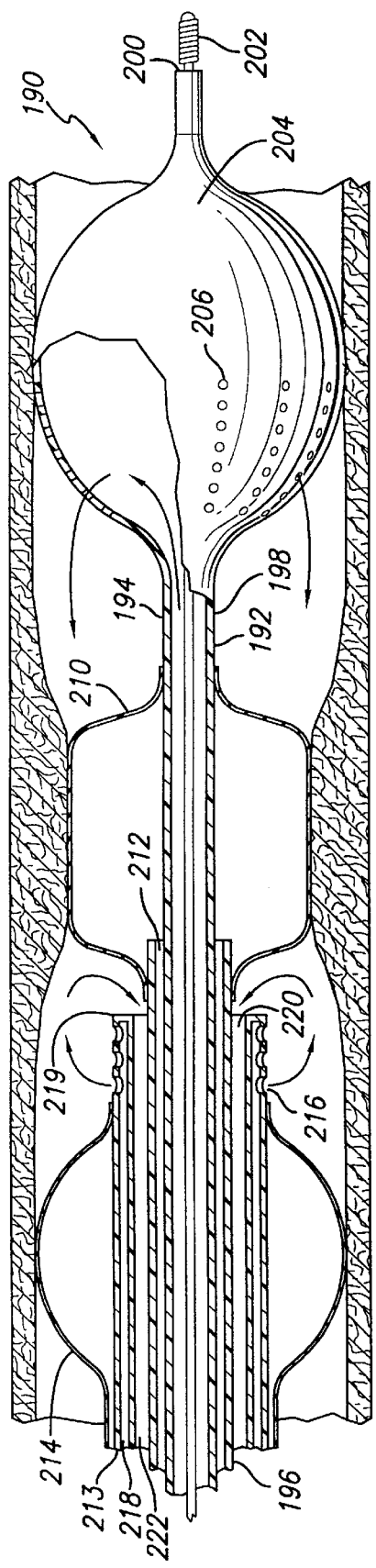

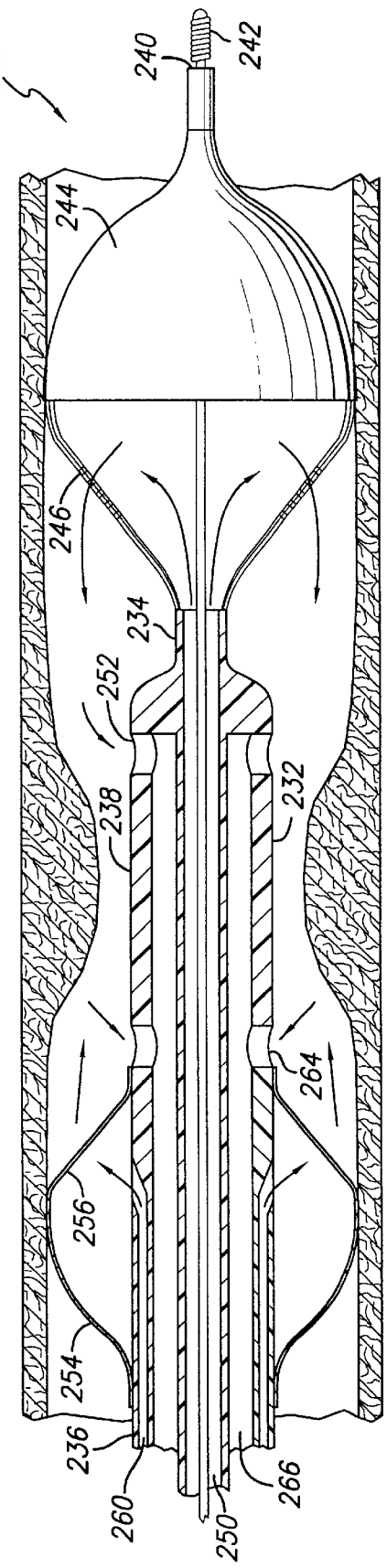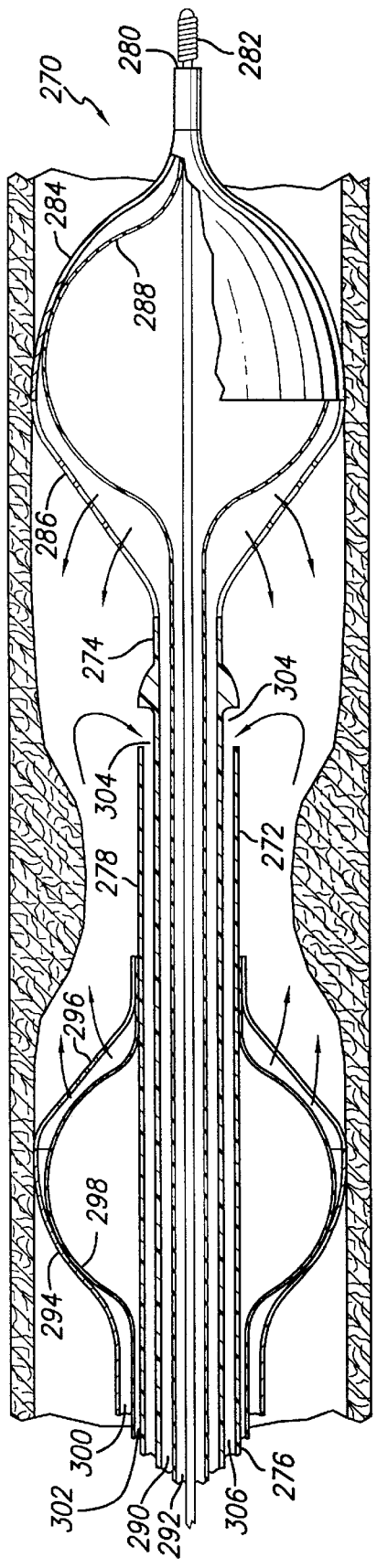

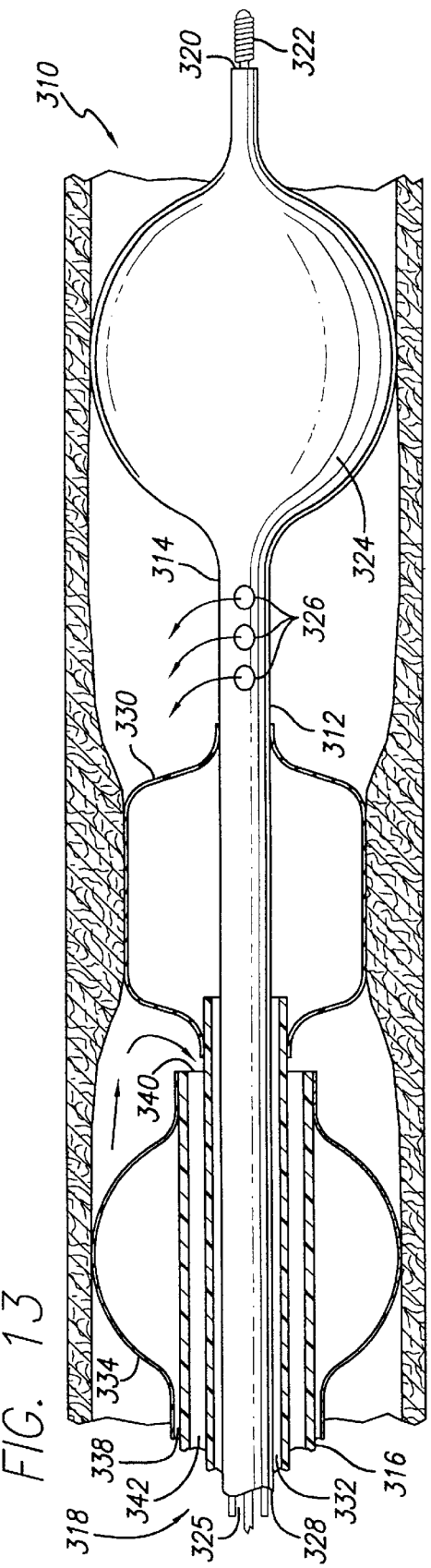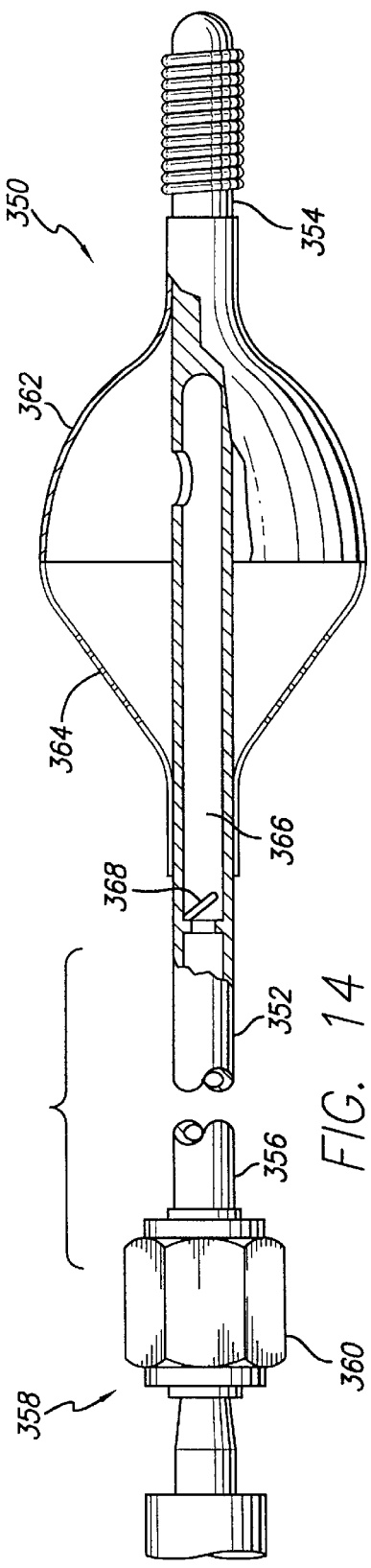
FIG. 13
FIG. 14

EMBOLI PROTECTION SYSTEM

BACKGROUND OF THE INVENTION

1. Field of the Invention

This invention relates generally to medical devices, and more particularly concerns systems and methods for containing, aspirating and removing emboli from blood vessels, and especially during interventional procedures treatment of cerebral blood vessels such as carotid arteries to prevent emboli or debris from entering and occluding downstream blood vessels leading to the brain which may cause a stroke.

2. Description of Related Art

A variety of non-surgical interventional procedures have been developed for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

In another widely practiced procedure, the stenosis can be treated by placing a device known as a stent into the stenosed region to hold open and sometimes expand the segment of blood vessel or other arterial lumen. Stents are particularly useful in the treatment of repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

However, it has been found that stenting and angioplasty, particularly angioplasty of the cerebral vessels such as the carotid arteries, and saphenous vein graft (SVG) angioplasty, for treating veins grafted in bypass surgery, which can become diseased and bring an increased risk of generating emboli, pose risks of dislodging thrombus or friable plaque, and that such a thrombus or plaque that is dislodged during such a procedure can enter the bloodstream and subsequently migrate through the patient's vasculature to sensitive organs such as the brain, where they may induce trauma. A thrombus or pieces of plaque material can be dislodged from a stenosis by expansion of the blood vessel being treated during a balloon angioplasty procedure and become released into the bloodstream. It has also been found that during deployment of a stent, it is possible for the stent to cut into the stenosis and shear off pieces of plaque which become embolic debris that can travel downstream and lodge in the patient's vascular system.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Filters have been developed for trapping and preventing such embolic debris from flowing through the vasculature. Such filters are usually delivered in a collapsed configuration through the patient's vasculature, and are then expanded once in place in the patient's blood vessel to trap emboli. After emboli have been trapped, the filter can again be collapsed to remove the filter with any trapped emboli from the vessel. However, it has been found that trapped emboli can escape from such filters during the time that the filters are being collapsed and removed from the blood vessels. In other instances, the rate of blood percolating through the filtering material may be slower than the normal blood flow which can either cause the filtering material to tear or cause the filter to dislodge from the deployed position due to the build up of fluid pressure behind the filter. Moreover, should the filter become clogged with debris, there is a possibility that blood circulation past the clogged filter will be insufficient for the downstream vessels and organs. If a filter should become clogged when in use in the carotid arteries, blood flow could be diminished to the vessels leading to the brain. While the brain may be capable of functioning for a short period of time without sufficient blood flow, blood stoppage of more than thirty to forty seconds could cause the patient to experience a seizure. If the physician administering the procedure is unaware that the filtering device is clogged and that there is little or no blood flowing to the brain, the injury to the patient can be as devastating as if an emboli itself had caused blockage of the cerebral arteries.

One emboli containment system is known in which a treatment chamber is formed within a blood vessel by occlusion balloons provided on catheters on opposite sides of a stenotic lesion to prevent emboli migration during a treatment procedure, with irrigation and aspiration within the chamber through catheter pathways to remove emboli from the treatment chamber. However, that have been emboli partially dislodged and that are not removed by such irrigation and aspiration can later become free to migrate into the rest of the vasculature. It would be desirable for such a containment system to provide for turbulent flow of fluid within such a treatment chamber within the chamber, such as by jetting or streaming of the fluid in order to more thoroughly remove emboli from within the treatment chamber that may only have become partially dislodged during the treatment procedure.

What has been needed and has been heretofore unavailable are systems and methods for containing, aspirating and removing emboli that have been dislodge and partially dislodged from blood vessels in conjunction with such interventional procedures as stenting and balloon angioplasty of blood vessels, for minimizing the risk of embolic migration during and after the interventional procedures. The present invention meets these and other needs.

SUMMARY OF THE INVENTION

Briefly, and in general terms, the present invention provides for a system and method for isolation of a section of a blood vessel to prevent migration of emboli from the section during an interventional procedure, and subsequent flushing of the section to remove any emboli dislodged during the procedure. As used in the description of the present invention, the terms "proximal" and "proximal direction" are intended to mean moving away from the heart of a patient or out of the patient, and the terms "distal" and "distal direction" are intended to mean moving toward the heart of a patient, or into the patient. These definitions will apply with reference to body lumens and apparatus, such as catheters, guide wires, and stents.

Accordingly, in one presently preferred embodiment, the present invention provides for an emboli protection system, comprising a distal blocking balloon catheter and a proximal blocking balloon catheter for isolating a portion of a blood vessel to be treated by an interventional procedure to prevent migration of emboli into the rest of the vasculature. The distal blocking balloon catheter preferably includes a shaft with an inflatable balloon mounted on the shaft near the distal end of the catheter, the shaft having at least one lumen for a guide wire device and at least one lumen for fluid communication with the inflatable balloon. The proximal blocking balloon catheter similarly includes a shaft with an inflatable balloon mounted on the shaft near the distal end of the catheter, the shaft having at least one lumen for a guide wire device and at least one lumen for fluid communication with the inflatable balloon for inflation of the inflatable balloon. In one presently preferred embodiment, the shaft of the proximal blocking balloon catheter is open ended, and preferably includes at least one lumen for fluid communication with the interior lumen of the portion of the blood vessel being treated.

In one presently preferred embodiment, the inflatable balloon of the distal blocking balloon catheter has a surface defining a plurality of perforations facing the proximal end of the catheter, and the inflatable balloon of the proximal blocking balloon catheter also has a surface defining a plurality of perforations facing away from the proximal end of the proximal blocking balloon catheter, to allow fluid supplied to the inflatable balloons to exit the perforations and flush emboli in the isolated portion of the blood vessel through the open end of the proximal blocking balloon catheter and proximally through the fluid communication lumen of the proximal blocking balloon catheter. In one alternate embodiment, the distal blocking balloon catheter can be incorporated with an interventional therapeutic device such as an angioplasty balloon catheter. In another alternate embodiment, the distal and blocking proximal balloon catheters can be incorporated with an interventional therapeutic device such as an angioplasty balloon catheter. In another presently preferred alternate embodiment, the inflation balloons of either or both of the distal and blocking proximal balloon catheters can be non-perforated, with an additional lumen being provided in either or both of the distal and proximal blocking catheters to supply fluid to flush emboli from the isolated portion of the blood vessel.

The present invention also provides for a method for removing emboli during arteriovenous interventional procedures with such a dual balloon emboli protection system having a distal blocking balloon catheter and a proximal blocking balloon catheter, by the steps of placing a guide wire across a lesion (or desired site), threading the distal blocking balloon catheter over the guide wire and placing the balloon of the distal blocking balloon catheter distal to the lesion, threading an interventional device such as an angioplasty balloon catheter over the shaft of the distal blocking balloon catheter and positioning the interventional device at the lesion site, and threading the proximal blocking balloon catheter over the angioplasty device and placing the proximal blocking catheter's balloon proximal to the lesion. The distal and proximal blocking balloons are then simultaneously inflated with an inflation fluid to block the portion of the blood vessel at both balloon sites, preferably with a low fluid pressure, such as 2–3 atm. for example, to isolate the lesion area from surrounding vasculature. When the balloons are perforated, the interventional device can be used to perform the angioplasty or similar interventional procedure, and then can be removed, without risking migration of emboli from the isolated portion of the blood vessel into the rest of the vasculature. The inflation fluid is then caused to stream out of the balloon perforations by increasing the pressure of the inflation fluid, which will, by a pressure differential that the fluid creates, flow through the open lumen of the proximal blocking balloon catheter and proximally through the proximal blocking balloon catheter out of the patient's body. The flow pressure between the proximal and distal blocking balloons can also be varied to cause corresponding changes in the flow direction and/or create additional turbulence in order to flush out any remaining emboli.

In another presently preferred embodiment, a source of thrombolytic inflation fluid is provided that is connected in fluid communication with the inflatable balloons of the distal and proximal blocking catheters, and the thrombolytic inflation fluid is used to inflate the distal and proximal blocking balloons simultaneously with the thrombolytic inflation fluid to block the artery at both balloon sites, and to cause the thrombolytic fluid to stream out of the balloon perforations and flow through the central lumen of the proximal blocking catheter and out of the patient's body, in order to break down and dissolve any thrombus and plaque in the isolated portion of the blood vessel through both the chemical effect of the drug and the streaming or jetting action of the fluid.

In an alternate preferred embodiment, the present invention provides for an emboli protection system for dissolving and removal of thrombus, stenotic or embolic material, that may be used during vascular interventional procedures or prior to such an interventional procedure for cleaning embolic material from a blood vessel, such as for cleaning a diseased saphenous vein graft prior to stenting of the graft. A blocking balloon catheter is provided, having a shaft with fixed distal and proximal inflatable balloons mounted near the distal end of the catheter. The blocking balloon catheter includes a shaft having one or more evacuation ports located between the distal and proximal balloons, and a lumen connected in fluid communication with the one or more evacuation ports for removing emboli through the proximal end of the catheter. The catheter also includes a lumen connected in fluid communication with the balloons for inflation of the balloons, and typically also have a lumen for a guide wire device. The distal and proximal balloons preferably have a surface defining a plurality of perforations, with the distal inflatable balloon having perforations facing the proximal end of the catheter, and the proximal balloon having perforations facing away from the proximal end of the catheter. Either or both of the inflatable balloons may also comprise a balloon-in-balloon configuration, with separate lumens being provided for inside and outside balloons. In such a balloon-in-balloon configuration, the inside balloon is non-perforated for use solely for inflation, while the outside balloon is provided with a surface defining a plurality of perforations, for drug delivery or flushing within an isolated portion of a blood vessel formed by inflation of the distal and proximal balloons, to allow simultaneous blocking of the blood vessel and flushing of emboli from the isolated portion of the blood vessel. In an alternate embodiment, one of the distal and proximal balloons may be non-perforated, and an additional lumen may be provided on the distal or proximal blocking catheter to supply a thrombolytic fluid to dissolve and remove thrombus, stenotic or other embolic material.

In the method of using the blocking balloon catheter with fixed distal and proximal inflatable balloons, the catheter is threaded over the guide wire to the desired location, and the distal and proximal balloons are preferably positioned on either side of the thrombotic or stenotic occlusion to be treated. Both balloons are then inflated to block the blood vessel, using a thrombolytic agent as the inflation fluid and under sufficient pressure to cause the thrombolytic inflation fluid to stream or jetting out of the perforations, to break down and dissolve the thrombus or plaque through both the chemical effect of the drug and the streaming or jetting action of the fluid ejected. Simultaneously, the drug and the thrombus, plaque or other embolic debris re evacuated from the site through the evacuation ports provided in the catheter.

In another presently preferred embodiment, the invention provides for triple balloon emboli protection system, comprising a guide wire or catheter shaft having a first, distal inflatable balloon mounted on the distal end of the guide wire or catheter shaft and at least one lumen for fluid communication with the distal balloon; a second, middle balloon mounted on the guide wire or catheter shaft proximal to the first inflatable balloon, such as for placing a stent, with the guide wire or catheter shaft having at least one lumen for fluid communication with the second, middle balloon; and a third inflatable balloon mounted on the guide wire or catheter shaft proximal to the second inflatable balloon, with the guide wire or catheter shaft having at least one lumen for fluid communication with the third balloon. The guide wire or catheter shaft is preferably provided with a fluid supply lumen with a port proximal to distal balloon to supply flushing fluid to flush emboli, and is preferably provided with an evacuation lumen with a port proximal to the second, middle balloon, for evacuation of flushing fluid and flushed emboli.

In a presently preferred method for using such a triple balloon emboli protection system for removing emboli during arteriovenous interventional procedures, such as angioplasty or placement of a stent, the guide wire is placed across a target site such as a lesion with the distal balloon distal to the lesion, the middle balloon at the site of the lesion, and the proximal balloon proximal to the lesion. The distal balloon is inflated with an inflation fluid to block the artery and isolate the lesion area from the surrounding vasculature, the middle balloon is inflated with an inflation fluid, such as to place a stent mounted on the middle balloon, and the proximal balloon is inflated to isolate the lesion area of the blood vessel from the rest of the vasculature. The middle balloon can then be deflated to release any emboli generated by placement of the stent, and can be reinflated and deflated to reduce the size of the lesion or stenosis at the target site, or to deploy or redeploy the stent evenly, or to a larger diameter. The proximal balloon can then be deflated, and fluid can be provided through the holes in the shaft proximal to the distal balloon for flushing emboli back through the artery for removal through a proximal connector device.

In another presently preferred embodiment, the invention provides for a single balloon emboli protection system, comprising a guide wire or catheter shaft having an inflatable balloon mounted on the distal end of the guide wire or catheter shaft and at least one lumen for fluid communication with the distal balloon. The proximal end of the shaft has a valve allowing for inflation and deflation of the balloon, which enables the balloon to remain dilated while the removable connector of a hemostatic valve, such as a rotating hemostatic valve, is gone. Infusion ports, holes or perforations are provided in the balloon facing the proximal end of the shaft, and are dimensioned to remain sealed until sufficient inflation fluid pressure is applied to the distal inflation balloon, in order to apply a pressure to the valve which will keep the valve closed when the connector is removed. The infusion holes are typically 0.001 to 0.002 inch in diameter. The action of the valve maintains a minimum pressure in the distal inflation balloon, allowing other devices to be introduced over the guide wire shaft during the procedure. Additional pressure can be provided to the distal inflation balloon to provide a flow of fluid through the infusion holes for providing a continuous flushing of the blood vessel proximal to the distal inflation balloon, which flows through the blood vessel, such as the external carotid artery, for example, back through a branching of the blood vessel, such as the carotid Y branching, for example, and performs aspiration by flushing emboli to another artery. The single balloon emboli protection system can be used in conjunction with currently compatible devices, such as balloon catheters, rapid exchange balloon catheters, stent delivery systems, guide wires, guiding catheters, angiographic catheters, and the like, and in particular can be used during vascular intervention, such as carotid artery angioplasty and stenting, in order to prevent stroke during carotid artery intervention.

In another presently preferred embodiment, the invention provides for an emboli protection system for isolating a portion of a blood vessel having a target site to be treated by an interventional procedure to prevent migration of emboli into the rest of the vasculature to permit perfusion and infusion of therapeutic drugs or fluid to the blood vessel being treated. The embolic protection comprises a blocking balloon catheter with a shaft having distal and proximal inflatable balloons, one or more guide wire lumens, and one or more lumens for fluid communication with the distal and proximal inflatable balloons. The shaft also includes one or more ports through the shaft proximal to the proximal balloon and one or more ports between the proximal and distal inflatable balloons, with the ports connected in fluid communication with the guide wire lumen to permit perfusion of blood to the isolated portion of the blood vessel through each the port between the proximal and distal blocking balloons. An inflation fluid supply is also connected in fluid communication with the distal and proximal inflatable balloons for supplying inflation fluid under pressure to the inflatable balloons under pressure for inflating the distal and proximal balloons in the blood vessel on either side of the target site to be treated, to isolate the selected portion of the blood vessel. In one presently preferred aspect, the guide wire lumen includes a distal opening, and a retractable guide wire device is disposed within the guide wire lumen, whereby the guide wire can be retracted from distal opening to permit perfusion of blood between the area of the blood vessel proximal to the proximal balloon to the area of the blood vessel distal to the distal balloon through the distal opening when the guide wire is retracted. In another presently preferred embodiment, a blocking balloon catheter is providing having a shaft with distal and proximal inflatable balloons, one or more guide wire lumens, one or more infusion lumens to allow infusion of therapeutic drugs or fluid, and one or more lumens for fluid communication with the distal and proximal inflatable balloons. The shaft includes one or more infusion ports through the shaft between the distal and proximal inflatable balloons, connected in fluid communication with the one or more infusion lumens to permit infusion of a therapeutic drug or fluid to the isolated portion of the blood vessel being treated. In another presently preferred aspect, one or more perfusion lumens can also be provided in the shaft, with one or more proximal perfusion ports through the shaft proximal to the proximal balloon, and one or more distal perfusion ports distal to the distal inflatable balloon, each of the perfusion ports connected in fluid communication with the one or more perfusion lumens to permit passive perfusion of blood flow between the proximal perfusion ports and the distal perfusion ports to the isolated portion of the blood vessel through each the port between the proximal and distal blocking balloons. In another presently preferred aspect, the shaft further comprises one or more distal infusion ports through the shaft distal to the distal inflatable balloon, connected in fluid communication with the one or more infusion lumens to permit infusion of therapeutic drugs or fluid through the one or more distal infusion ports.

These and other aspects and advantages of the invention will become apparent from the following detailed description and the accompanying drawings, which illustrate by way of example the features of the invention.

BRIEF DESCRIPTION OF THE DRAWINGS

FIG. 3 is a sectional view showing a proximal blocking balloon catheter placed over the angioplasty balloon catheter of FIG. 2, with the proximal blocking balloon placed proximal to the target site to be treated;

FIG. 4 is a sectional view showing the distal blocking balloon catheter and proximal blocking balloon catheter of FIG. 3, with the angioplasty balloon catheter withdrawn following an angioplasty procedure, for flushing of emboli from the isolated portion of the blood vessel;

FIG. 5 is a sectional view showing a distal blocking balloon catheter having an angioplasty balloon incorporated with the distal blocking balloon catheter in a second embodiment of an emboli protection system for isolating a portion of a blood vessel to be treated, showing the distal blocking balloon placed distal to a target site to be treated and the angioplasty balloon placed at the target site to be treated;

FIG. 6 is a sectional view showing a proximal blocking balloon catheter placed over the distal blocking balloon catheter of FIG. 5, with the distal blocking balloon and the proximal blocking balloon placed on either side of the angioplasty balloon and target site to be treated;

FIG. 7 is a sectional view similar to FIG. 6, showing the distal and proximal blocking balloon catheters in position with the distal and proximal balloons on either side of the target site following an angioplasty procedure for flushing of emboli from the isolated portion of the blood vessel treated;

FIG. 8 is a sectional view of a third embodiment of an emboli protection system for isolating a portion of a blood vessel to be treated, with a distal blocking balloon catheter having an angioplasty balloon and proximal balloon incorporated with the distal blocking balloon catheter, the distal and proximal blocking balloons shown placed on either side of a target site to be treated and the angioplasty balloon placed at the target site to be treated;

FIG. 9 is a sectional view of a fourth embodiment of an emboli protection system of the invention in which the inflation balloon of the distal blocking balloon catheter is non-perforated, with one or more ports and a lumen being provided in the distal blocking catheter to supply fluid to flush emboli from the isolated portion of the blood vessel;

FIG. 10 is a sectional view of a fifth embodiment of an emboli protection system of the invention in which the inflation balloon of the proximal blocking balloon catheter is non-perforated, with one or more ports and a lumen being provided in the proximal blocking catheter to supply fluid to flush emboli from the isolated portion of the blood vessel;

FIG. 11 is a sectional view of a sixth embodiment of an emboli protection system of the invention in which a blocking balloon catheter with distal and proximal balloons includes a shaft having one or more evacuation ports of an evacuation lumen for removing emboli through the proximal end of the catheter;

FIG. 12 is a sectional view of a seventh embodiment of an emboli protection system of the invention similar to that of FIG. 11, in which the inflatable balloons have a balloon-in-balloon configuration, with separate lumens being provided for inside and outside balloons;

FIG. 13 is a sectional view of an eighth embodiment of an emboli protection system of the invention in which a catheter shaft is provided with distal, middle, and proximal inflatable balloons mounted on the distal end of the catheter shaft;

FIG. 14 is a sectional view of a ninth embodiment of an emboli protection system of the invention in which a guide wire shaft is provided with an inflatable balloon mounted on the distal end of the guide wire shaft, a lumen for fluid communication with the distal balloon, and a one way valve in the proximal end of the shaft;

DETAILED DESCRIPTION OF THE PREFERRED EMBODIMENTS

Vascular interventional procedures for treatment of stenotic regions of blood vessels, such as balloon angioplasty and implantation of a stent typically compress at least a portion of the stenotic region and press the vessel wall radially outward to increase the interior flow passage of the blood vessel. These and other types of vascular interventional procedures for treatment of stenotic regions of blood vessels can entail the risk of dislodging thrombus or friable plaque. The use of such procedures for treatment of the cerebral vessels, such as the carotid arteries, and saphenous vein grafts, can particularly involve increased risks that such a thrombus or plaque may be dislodged during such a procedure, enter the bloodstream, and subsequently become lodged in the brain, or in other sensitive organs. While approaches such as cutting emboli into smaller pieces, filtration of the emboli, and removing of embolic debris by suction have been proposed.

One emboli containment system is known in which a treatment chamber is formed within a blood vessel by occlusion balloons provided on catheters on opposite sides of a stenotic lesion to prevent emboli migration during a treatment procedure, with irrigation and aspiration within the chamber through catheter pathways to remove emboli from the treatment chamber. However, emboli that have been partially dislodged and that are not removed by such irrigation and aspiration can later become free to migrate into the rest of the vasculature. It would be desirable to provide an improved containment system to provide for a more thorough flushing of such an isolated area within a blood vessel in order to more thoroughly remove emboli from within the treatment chamber that may only have become partially dislodged during the treatment procedure.

What has been needed and has been heretofore unavailable are improved systems and methods for containing, aspirating and removing emboli that have been dislodge and partially dislodged from blood vessels in conjunction with such interventional procedures as stenting and balloon angioplasty of blood vessels, for minimizing the risk of embolic migration during and after the interventional procedures.

Figure 1:
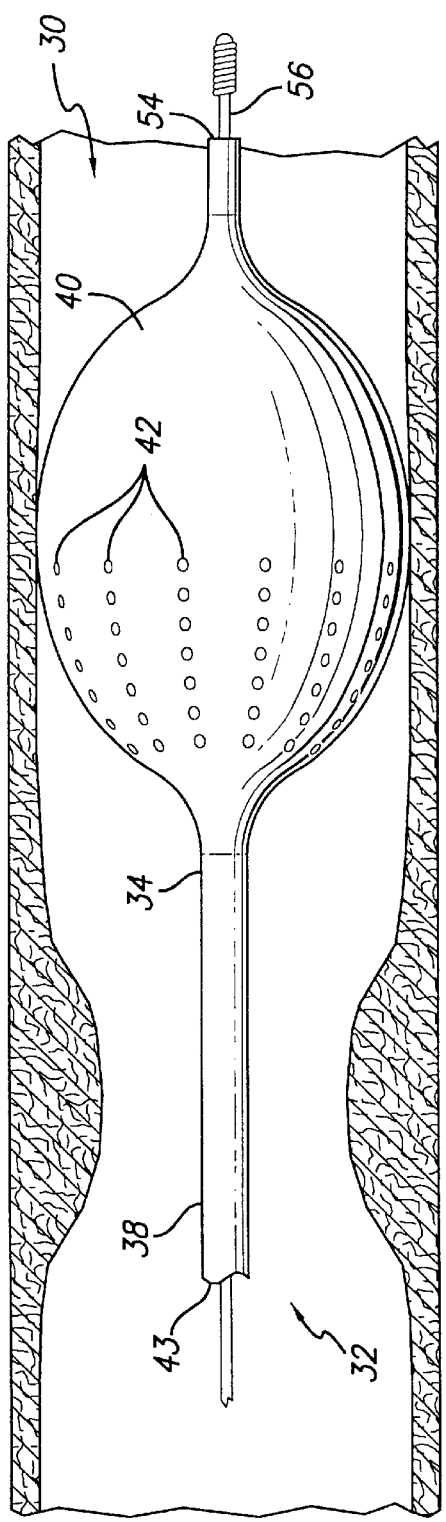
FIG. 1 is a perspective cutaway view of a distal blocking balloon catheter of a first embodiment of an emboli protection system for isolating a portion of a blood vessel to be treated, showing the distal blocking balloon placed distal to a target site to be treated.

As is illustrated in the drawings, in a first embodiment, the invention provides for a dual balloon emboli protection system for isolating a portion of a blood vessel to be treated and removing emboli from the isolated portion of the blood vessel. With reference to FIG. 1, the dual balloon emboli protection system 30 includes a distal blocking catheter 32 having a distal end 34 and a proximal end (not shown), and a shaft 38. A distal inflatable balloon 40 is mounted on or near the distal end of the shaft, having a plurality of perforations 42 formed in the surface of the distal inflatable balloon facing the proximal end of catheter. The distal inflatable balloon of the distal balloon catheter can be introduced into the vasculature and placed in distal to the target site in the blood vessel to be treated, and inflation fluid can be provided to the distal inflatable balloon through an inflation fluid lumen 43 of the shaft of the distal blocking catheter to inflate the distal balloon. The shaft of the distal blocking balloon catheter also preferably has at least one lumen 54 for a guide wire device 56.

The perforations of the distal inflatable balloon are preferably dimensioned so that the perforations remain closed up to a predetermined low pressure of the inflation fluid, so that the distal inflatable balloon can be inflated to occlude the blood vessel, and so that when inflation fluid is supplied at a pressure above said predetermined low pressure, the perforations will open so as to release the inflation fluid to jet or stream proximally away from the distal inflatable balloon. The diameter of the perforations in the distal inflatable balloon is currently preferably from about 10 to about 150 microns, and can range typically in number from several dozen to several thousand. The distal inflatable balloon can be made of low or high compliance material, and may have a cylindrical, oval, square or rectangular shape. As is further explained below, in an alternate preferred embodiment, the distal inflatable balloon may be non-perforated, and an additional lumen can be provided on the distal blocking catheter to supply fluid to flush emboli.

Figure 2:
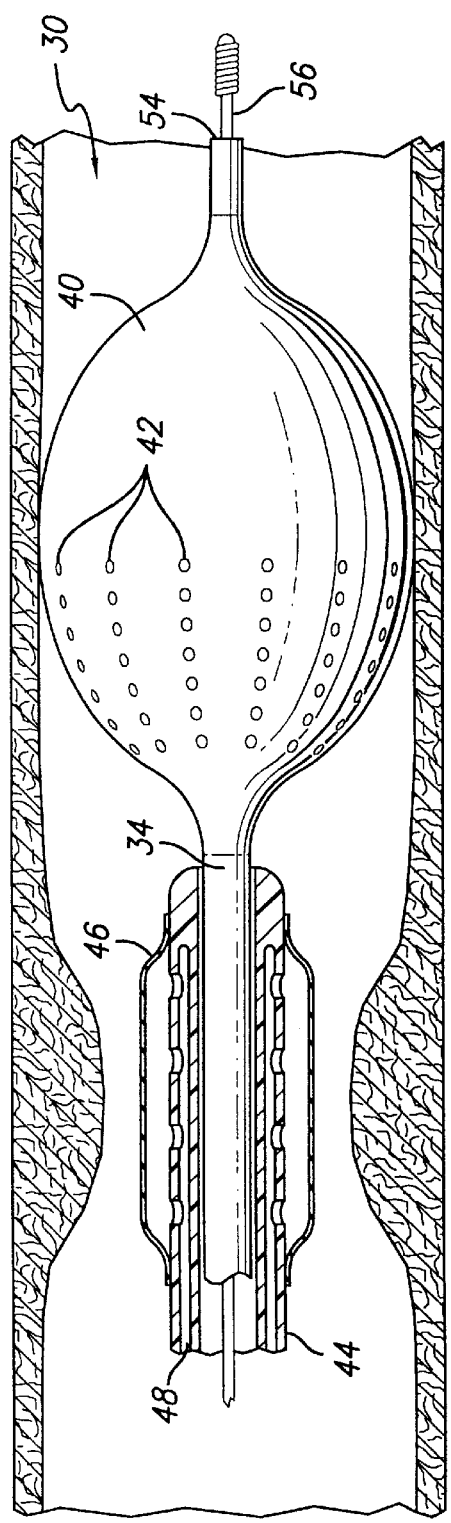
FIG. 2 is a sectional view showing an angioplasty balloon catheter placed over the distal blocking balloon catheter of FIG. 1, with the angioplasty balloon placed at the target site to be treated.

Referring to FIG. 2, an interventional device such as an angioplasty balloon catheter 44 can be introduced into the vasculature and to the target site to be treated over the distal blocking balloon catheter. The interventional device may also be another therapeutic device such as a stent, a combination of a stent and balloon, or a balloon to deliver drugs, for example. The angioplasty balloon catheter preferably carries an angioplasty balloon 46 mounted on or near the distal end of the angioplasty balloon catheter, which preferably has an interior lumen 48 connected in fluid communication with the angioplasty balloon for inflation and deflation of the angioplasty balloon.

As is illustrated in FIG. 3, a proximal blocking catheter 50, carrying an inflatable balloon 51 mounted on or near the distal end of the proximal blocking catheter, can be placed over the angioplasty balloon catheter, with the proximal blocking balloon placed proximal to the target site to be treated. In an alternate preferred embodiment, the proximal blocking catheter may be a guiding catheter with a balloon mounted on or near the distal end of the guiding catheter, and with an additional lumen provided to supply fluid for balloon inflation. The inflatable balloon of the proximal blocking catheter also preferably has a plurality of perforations 52 defined in the surface of the proximal balloon facing away from the proximal end of the catheter, or toward the distal end of the catheter and toward the target site to be treated. The inflatable balloon of the proximal blocking catheter can be made of low or high compliance material, and can have a cylindrical, oval, square or rectangular shape. As is explained further below, in a preferred alternate embodiment, the proximal blocking catheter may carry an inflatable balloon that is non-perforated, and an additional lumen can be provided in the proximal blocking catheter to supply fluid to flush emboli.

In a presently preferred aspect of the invention, the proximal blocking catheter shaft is open ended, having an evacuation port 60, with at least one lumen 62 for fluid communication and emboli evacuation proximally through the proximal blocking catheter, and having at least one lumen 64 for balloon inflation. The perforations of the proximal inflatable balloon are preferably dimensioned so that the perforations remain closed up to a predetermined low pressure of the inflation fluid, so that the proximal inflatable balloon can be inflated to occlude the blood vessel, and so that when inflation fluid is supplied at a pressure above the predetermined low pressure, the perforations will open so as to release the inflation fluid to jet or stream distally away from the proximal inflatable balloon. The diameter of the perforations in the proximal inflatable balloon is currently preferably from about 10 to about 150 microns, and can range typically in number from several dozen to several thousand.

As is illustrated in FIG. 4, the angioplasty balloon catheter can be withdrawn following an angioplasty procedure, for flushing of emboli from the isolated portion of the blood vessel by raising the pressure of the inflation fluid above the pressure required to open the perforations of the distal and proximal inflatable balloons, to cause the inflation fluid to jet or stream out of the perforations toward the target site to be treated and to carry emboli and embolic debris along to be evacuated through the evacuation port in the proximal blocking catheter. A suitable angioplasty balloon is currently preferably formed of a non-compliant balloon material, such as nylon or polyethylene terephthalate (PET) for example, or other similar balloon materials, although other balloon materials such as elastic, compliant latex or polyurethane, or other similar balloon materials, may also be suitable.

With reference to FIG. 5, in a second alternate embodiment of an emboli protection system 70 for isolating a portion of a blood vessel to be treated, a distal blocking balloon catheter 72 may be provided with an interventional device 86 such as an angioplasty balloon incorporated with the blocking balloon catheter. The angioplasty balloon can be attached to the blocking balloon catheter such as by adhesive, laser bonding, heat bonding, or solvent bonding, for example. The distal blocking balloon catheter has a distal end 74, a proximal end 76, and a shaft 78, having a distal inflatable balloon 80 mounted on or near the distal end of the blocking balloon catheter, and at least one lumen 81 for inflation and deflation of the distal inflatable balloon. Alternatively, the interventional device may be another therapeutic device such as a stent, a combination of a stent and balloon, or a balloon to deliver drugs, for example.

The distal inflatable balloon 80 preferably has a plurality of perforations 82, generally shown in FIGS. 5 and 6, and as shown in FIGS. 1–4 of the previous embodiment, formed in the proximal surface of the distal inflatable balloon facing the proximal end of catheter. The distal blocking balloon catheter preferably includes at least one distal evacuation port 87 and at least one lumen 89 for fluid communication with the distal evacuation port for evacuation of fluid injected through the perforations in the distal inflatable balloon proximally through the distal blocking balloon catheter. The distal inflatable balloon of the distal balloon catheter can be introduced into the vasculature and placed in distal to the target site in the blood vessel to be treated, and inflation fluid can be provided to the distal inflatable balloon through the inflation fluid lumen of the shaft of the distal blocking catheter to inflate the distal balloon. In this embodiment, an angioplasty balloon 86 is mounted to the distal blocking catheter proximal to the distal inflatable balloon, and an interior lumen 88 is connected in fluid communication with the angioplasty balloon for inflation and deflation of the angioplasty balloon. The distal evacuation port and lumen of the distal blocking balloon catheter prevents pressure from building up within the distal chamber formed in the blood vessel between the distal balloon and the angioplasty balloon, allowing a higher fluid pressure to be applied within the angioplasty balloon than within the distal chamber, so that the angioplasty balloon can be properly inflated. The angioplasty balloon is currently preferably formed of a non-compliant balloon material, such as nylon or polyethylene terephthalate (PET) for example, or other similar balloon materials, although other balloon materials such as elastic, compliant latex or polyurethane, or other similar balloon materials, may also be suitable. The distal blocking balloon catheter also preferably has at least one lumen 94 for a guide wire device 96.

The perforations of the distal inflatable balloon are preferably dimensioned so that the perforations remain closed up to a predetermined low pressure of the inflation fluid, so that the distal inflatable balloon can be inflated to occlude the blood vessel, and so that when inflation fluid is supplied at a pressure above said predetermined low pressure, the perforations will open so as to release the inflation fluid to jet or stream proximally away from the distal inflatable balloon. The diameter of the perforations in the distal inflatable balloon is currently preferably from about 10 to about 150 microns, and can range typically in number from several dozen to several thousand. The distal inflatable balloon can be made of low or high compliance material, and may have a cylindrical, oval, square or rectangular shape. As is further explained below, in an alternate preferred embodiment, the distal inflatable balloon may be non-perforated, and an additional lumen can be provided on the distal blocking catheter to supply fluid to flush emboli.

Referring to FIG. 6, a proximal blocking balloon catheter 90 carrying an inflatable balloon 91 may be introduced and placed over the distal blocking balloon catheter, with the distal blocking balloon and the proximal blocking balloon placed on either side of the angioplasty balloon and target site to be treated prior to an angioplasty procedure. In an alternate preferred embodiment, the proximal blocking catheter may be a guiding catheter with a balloon mounted on or near the distal end of the guiding catheter, and with an additional lumen provided to supply fluid for balloon inflation. The inflatable balloon of the proximal blocking catheter also preferably has a plurality of perforations 92 defined in the distal surface of the proximal balloon facing away from the proximal end of the catheter, or toward the distal end of the catheter and toward the target site to be treated, as illustrated in FIGS. 5 and 6, and as shown in FIGS. 3 and 4 of the previous embodiment. The inflatable balloon of the proximal blocking catheter can be made of low or high compliance material, and can have a cylindrical, oval, square or rectangular shape. As is explained further below, in a preferred alternate embodiment, the proximal blocking catheter may carry an inflatable balloon that is non-perforated, and an additional lumen can be provided in the proximal blocking catheter to supply fluid to flush emboli.

In a presently preferred aspect of the invention, the proximal blocking catheter shaft is open ended, having an evacuation port 100, at least one lumen 102 for inflation of the proximal balloon, and having at least one lumen 104 for fluid communication and emboli evacuation proximally through the proximal blocking balloon catheter. The perforations of the proximal inflatable balloon are preferably dimensioned so that the perforations remain closed up to a predetermined low pressure of the inflation fluid, so that the proximal inflatable balloon can be inflated to occlude the blood vessel, and so that when inflation fluid is supplied at a pressure above the predetermined low pressure, such as following an angioplasty procedure, as shown in FIG. 7, the perforations will open so as to release the inflation fluid to jet or stream distally away from the proximal inflatable balloon. The diameter of the perforations in the proximal inflatable balloon is currently preferably from about 10 to about 150 microns, and can range typically in number from several dozen to several thousand.

A third alternate embodiment of an emboli protection system 110 for isolating a portion of a blood vessel to be treated is illustrated in FIG. 8, with a blocking balloon catheter 112 having an interventional device, such as an angioplasty balloon, and a proximal balloon incorporated with the distal blocking balloon catheter. The angioplasty balloon and proximal balloon can be attached to the distal blocking balloon catheter such as by adhesive, laser bonding, heat bonding, or solvent bonding, for example. The interventional device may also be another therapeutic device such as a stent, a combination of a stent and balloon, or a balloon to deliver drugs, for example. The blocking balloon catheter has a distal end 114, a proximal end 116, and a shaft 118 having at least one lumen 120 for a guide wire device 122. A distal inflatable balloon 124 is mounted on or near the distal end of the shaft, and in a currently preferred embodiment, the distal inflatable balloon has a plurality of perforations 126 through the balloon facing the proximal end of catheter. The distal inflatable balloon may be made of low or high compliance material, and may have a cylindrical, oval, square or rectangular shape. The perforations of the distal inflatable balloon are preferably dimensioned so that the perforations remain closed up to a predetermined low pressure of the inflation fluid, so that the distal inflatable balloon can be inflated to occlude the blood vessel, and so that when inflation fluid is supplied at a pressure above said predetermined low pressure, the perforations will open so as to release the inflation fluid to jet or stream proximally away from the distal inflatable balloon. The diameter of the perforations in the distal inflatable balloon is currently preferably from about 10 to about 150 microns, and can range typically in number from several dozen to several thousand. As is further explained below, in an alternate preferred embodiment, the distal inflatable balloon may be non-perforated, and an additional lumen can be provided on the distal blocking catheter to supply fluid to flush emboli.

An angioplasty balloon 130 is also preferably mounted to the shaft of the blocking balloon catheter proximal to the distal inflatable balloon. The angioplasty balloon is currently preferably formed of a non-compliant balloon material, such as nylon or polyethylene terephthalate (PET) for example, or other similar balloon materials, although other balloon materials such as elastic, compliant latex or polyurethane, or other similar balloon materials, may also be suitable. An interior lumen 132 is provided in the shaft that is connected in fluid communication with the angioplasty balloon for inflation and deflation of the angioplasty balloon. A proximal inflatable balloon 134 is also preferably mounted to the shaft of the blocking balloon catheter proximal to the angioplasty balloon. The proximal inflatable balloon of the proximal blocking catheter also preferably has a plurality of perforations 136 defined in the surface of the proximal balloon facing away from the proximal end of the catheter, or toward the distal end of the catheter and toward the target site to be treated. The perforations of the proximal inflatable balloon are preferably dimensioned so that the perforations remain closed up to a predetermined low pressure of the inflation fluid, so that the proximal inflatable balloon can be inflated to occlude the blood vessel, and so that when inflation fluid is supplied at a pressure above the predetermined low pressure, such as following an angioplasty procedure, the perforations will open so as to release the inflation fluid to jet or stream distally away from the proximal inflatable balloon. The diameter of the perforations in the proximal inflatable balloon is currently preferably from about 10 to about 150 microns, and can range typically in number from several dozen to several thousand.

An inflation lumen 138 is provided in the blocking balloon catheter for fluid communication with the proximal inflatable balloon, and the catheter shaft preferably has an evacuation port 140, and at least one lumen 142 for fluid communication and emboli evacuation. The inflatable balloon of the proximal blocking catheter can be made of low or high compliance material, and can have a cylindrical, oval, square or rectangular shape. As is explained further below, in a preferred alternate embodiment, the proximal blocking catheter may carry an inflatable balloon that is non-perforated, and an additional lumen can be provided in the blocking balloon catheter to supply fluid to flush emboli.

In a fourth currently preferred embodiment of an emboli protection system 150 of the invention, as illustrated in FIG. 9, the inflation balloon of the distal blocking balloon catheter can be non-perforated, with an additional port and lumen being provided in the distal blocking catheter to supply fluid to flush emboli from the isolated portion of the blood vessel. In this embodiment, a distal blocking balloon catheter 152 is provided, having a distal end 154 and a proximal end 156. The distal blocking balloon catheter includes a shaft 158 having at least one lumen 160 for a guide wire device 162. A distal inflatable balloon 164 is mounted on or near the distal end of the shaft of the distal blocking balloon catheter, with at least one lumen 165 for fluid communication with and inflation and deflation of the distal balloon. A plurality of perforations or ports 166 are provided through the distal end of catheter proximal to the distal inflatable balloon, with lumen 167 connected in fluid communication with the perforations or ports to supply fluid to flush emboli from the isolated portion of the blood vessel. The diameter of the perforations is currently preferably from about 10 to about 150 microns, and can range typically in number from several dozen to several thousand.

An interventional device such as an angioplasty catheter 168 carrying an angioplasty balloon 170 can be introduced over the blocking balloon catheter, with the angioplasty catheter having an interior lumen 172 provided in the catheter shaft connected in fluid communication with the angioplasty balloon for inflation and deflation of the angioplasty balloon. The angioplasty balloon is currently preferably formed of a non-compliant balloon material, such as nylon or polyethylene terephthalate (PET) for example, or other similar balloon materials, although other balloon materials such as elastic, compliant latex or polyurethane, or other similar balloon materials, may also be suitable. The interventional device may also be another therapeutic device such as a stent, a combination of a stent and balloon, or a balloon to deliver drugs, for example.

The distal inflatable balloon of the distal blocking balloon catheter can thus be introduced into the vasculature and placed in distal to the target site in the blood vessel to be treated and with the angioplasty balloon at the target site to be treated, and inflation fluid can be provided to the distal inflatable balloon to inflate the distal balloon. A proximal blocking balloon catheter 173 is also provided, with a proximal inflatable balloon 174 mounted on or near the distal end of the proximal blocking balloon catheter, and having a plurality of perforations 176 defined in the proximal balloon facing away from the proximal end of the catheter, or distally toward the target site to be treated. An inflation lumen 178 is preferably provided in the proximal blocking balloon catheter for fluid communication with the proximal inflatable balloon, and the proximal blocking balloon catheter shaft preferably has an evacuation port 180, with at least one lumen 182 for fluid communication and emboli evacuation. The perforations of the distal blocking balloon catheter and the proximal balloon are preferably dimensioned so that the perforations remain closed up to a predetermined low pressure of the inflation fluid, so that the distal and proximal inflatable balloons can be inflated to occlude the blood vessel, and so that when inflation fluid is supplied at a pressure above said predetermined low pressure, the perforations will open so as to release the inflation fluid to jet or stream between the proximal and distal balloons and toward the target site. The diameter of the perforations in the proximal inflatable balloon is currently preferably from about 10 to about 150 microns, and can range typically in number from several dozen to several thousand. The distal and proximal inflatable balloons can be made of low or high compliance material, and can have a cylindrical, oval, square or rectangular shape.

Referring to FIG. 10, a fifth alternate embodiment of an emboli protection system 190 of the invention is illustrated, in which the inflation balloon of the proximal blocking balloon catheter is non-perforated. In this embodiment, the distal blocking balloon catheter 192 is shown having a distal end 194, a proximal end 196, and a catheter shaft 198 having at least one lumen 200 for a guide wire device 202, with a distal inflatable balloon 204 mounted at or near the distal end of the catheter shaft. A plurality of perforations 206 are formed in the distal inflatable balloon that face the proximal end of catheter. The perforations of the distal inflatable balloon are preferably dimensioned so that the perforations remain closed up to a predetermined low pressure of the inflation fluid, so that the distal inflatable balloon can be inflated to occlude the blood vessel, and so that when inflation fluid is supplied at a pressure above the predetermined low pressure, such as following an angioplasty procedure, the perforations will open so as to release the inflation fluid to jet or stream distally away from the proximal inflatable balloon. The diameter of the perforations in the distal inflatable balloon is currently preferably from about 10 to about 150 microns, and can range typically in number from several dozen to several thousand.

An interventional device such as an angioplasty balloon 210 is also mounted to the blocking balloon catheter, with the catheter shaft having an interior lumen 212 connected in fluid communication with the angioplasty balloon for inflation and deflation of the angioplasty balloon. The angioplasty balloon is currently preferably formed of a non-compliant balloon material, such as nylon or polyethylene terephthalate (PET) for example, or other similar balloon materials, although other balloon materials such as elastic, compliant latex or polyurethane, or other similar balloon materials, may also be suitable. The interventional device may also be another therapeutic device such as a stent, a combination of a stent and balloon, or a balloon to deliver drugs, for example.

As is illustrated in FIG. 10, a proximal blocking balloon catheter 213 is also provided, having a proximal inflatable balloon 214 at or near the distal end of the proximal blocking balloon catheter. The proximal inflatable balloon is non-perforated, with one or more additional ports or perforations 216 being provided in the proximal blocking balloon catheter distal to the proximal inflatable balloon, and an inflation lumen 218 for the proximal inflatable balloon provided in the proximal blocking balloon catheter for inflating the proximal inflatable balloon and for supplying fluid to flush emboli from the isolated portion of the blood vessel. The diameter of the perforations is currently preferably from about 10 to about 150 microns. The proximal blocking balloon catheter shaft 219 preferably has an evacuation port 220 and at least one lumen 222 for fluid communication and emboli evacuation. In an alternate implementation of the invention, the proximal blocking balloon catheter may also be non-perforated, with an additional lumen and one or more corresponding outlet ports being provided on the distal or proximal blocking catheter to supply fluid to flush emboli. The distal and proximal inflatable balloons can be made of low or high compliance material, and can have a cylindrical, oval, square or rectangular shape.

Referring to the embodiments of the dual balloon emboli protection system of FIGS. 1 to 10, a preferred method of operation of such a dual balloon emboli protection system involves providing such a distal blocking catheter and a proximal blocking catheter, with the distal blocking catheter having a distal inflatable balloon, and the proximal blocking catheter having an inflatable balloon, for removing emboli during angioplasty or other types of arteriovenous interventional procedures, involves initially placing a guide wire across a lesion or other desired target site within a blood vessel to be treated. The catheter bearing the distal inflatable blocking balloon can then be threaded over the guide wire to place the distal inflatable blocking balloon distal to the lesion, and an interventional device such as an angioplasty balloon catheter can be positioned at the lesion site, either as the distal inflatable blocking balloon is placed, or subsequently thereto by threading the interventional device over the catheter carrying the distal inflatable blocking balloon, where the interventional device is provided on a separate catheter. The proximal blocking balloon catheter is placed proximal to the lesion, either as the distal inflatable blocking balloon and interventional device are placed, or subsequently thereto by threading the interventional device over the catheter carrying the interventional device, where the interventional device is provided on a catheter separate from that carrying the proximal inflatable balloon.

The distal and proximal blocking balloons are then simultaneously inflated with an inflation fluid to block the portion of the blood vessel or artery being treated at both the proximal and distal balloon sites, preferably with a low fluid pressure that will not cause the inflation fluid to stream out the perforations in the balloons and/or in either of the catheters carrying the distal and proximal inflatable balloons, such as 2–3 atm. for example, to block fluid flow through the blood vessel and isolate the lesion area from surrounding vasculature. When the interventional device is carried on a catheter separate and independent from that carrying the distal and/or proximal inflatable balloons, the interventional device can be used to perform the angioplasty or similar interventional procedure, and then can be removed while leaving the distal and proximal inflatable balloons in position in an inflated condition, without risking migration of emboli from the isolated portion of the blood vessel into the rest of the vasculature. The pressure of the inflation fluid can be increased to create a pressure differential between inflation fluid in the blocking balloon catheter proximal and distal inflation balloons and the pressure within the isolated portion of the blood vessel to cause the inflation fluid to jet or stream out of the balloon perforations, which can dislodge and carry emboli from the isolated portion of the blood vessel to exit through the open evacuation lumen near the proximal balloon, and proximally out of the patient's body. The flow pressure between the proximal and distal blocking balloons can also be varied to cause corresponding changes in the flow direction and/or create additional turbulence in order to flush out any remaining emboli.

It should be readily apparent that in the foregoing embodiments, the proximal inflatable balloon does not need to be open ended to provide an evacuation port, such as if the proximal inflatable balloon is to be incorporated with a distal blocking balloon catheter or with an angioplasty catheter, for example, since one or more evacuation ports can also be provided in the distal blocking balloon catheter, angioplasty catheter or other type of interventional catheter, or in the proximal blocking balloon catheter. It should also be readily apparent that although in the foregoing embodiments the distal blocking balloon catheter has been described as being open ended because the catheter is to be threaded over a guide wire, the distal blocking balloon catheter could alternatively include a fixed guide wire. It should also be readily apparent that the inflation fluid used may be a thrombolytic fluid, so that a source of thrombolytic inflation fluid can be provided that is connected in fluid communication with the inflatable balloons of the distal and proximal blocking catheters, and the thrombolytic inflation fluid can thus be used to inflate the distal and proximal blocking balloons simultaneously with the thrombolytic inflation fluid to block the artery at both balloon sites, to cause the thrombolytic fluid to stream out of the balloon perforations and flow through the central lumen of the proximal blocking catheter and out of the patient's body, in order to break down and dissolve any thrombus and plaque in the isolated portion of the blood vessel through both the chemical effect of the drug and the streaming or jetting action of the fluid.

Referring to FIG. 11, in a sixth alternate embodiment, the present invention provides for an emboli protection system 230 in which a blocking balloon catheter is provided with distal and proximal balloons, and including a shaft having one or more evacuation ports of an evacuation lumen for removing emboli through the proximal end of the catheter. The blocking balloon catheter 232 has a distal end 234, a proximal end 236, and a shaft 238 having at least one lumen 240 for a guide wire device 242. A distal inflatable balloon 244 is mounted on the shaft approximately at or near the distal end of the catheter. A plurality of perforations 246 are formed in the distal inflatable balloon facing the proximal end of catheter, and an interior lumen 250 in the catheter shaft is connected in fluid communication with the distal balloon for inflation and deflation of the distal balloon. The catheter shaft preferably has one or more removal or evacuation ports 252 adjacent to the distal balloon, and at least one lumen 266 connected to the distal evacuation port or ports for fluid communication and emboli evacuation. The number of distal evacuation ports typically can range from 1 to 5. The perforations of the distal inflatable balloon are preferably dimensioned so that the perforations remain closed up to a predetermined low pressure of the inflation fluid, so that the distal inflatable balloon can be inflated to occlude the blood vessel, and so that when inflation fluid is supplied at a pressure above the predetermined low pressure, such as following an angioplasty procedure, the perforations will open so as to release the inflation fluid to jet or stream distally away from the proximal inflatable balloon. The diameter of the perforations in the distal inflatable balloon is currently preferably from about 10 to about 150 microns, and can range typically in number from several dozen to several thousand.

A proximal inflatable balloon 254 is also preferably mounted to the shaft of the blocking balloon catheter proximal to the distal inflatable balloon. The proximal inflatable balloon of the blocking balloon catheter also preferably has a plurality of perforations 256 defined in the distal surface of the proximal balloon facing away from the proximal end of the catheter, or toward the distal end of the catheter and toward the target site to be treated. Alternatively, the proximal balloon may be non-perforated, with an additional lumen being provided with one or more ports on the catheter shaft between the distal and proximal inflatable balloons to supply fluid to flush emboli. The perforations of the proximal inflatable balloon are preferably dimensioned so that the perforations remain closed up to a predetermined low pressure of the inflation fluid, so that the proximal inflatable balloon can be inflated to occlude the blood vessel, and so that when inflation fluid is supplied at a pressure above the predetermined low pressure, the perforations will open so as to release the inflation fluid to jet or stream distally away from the proximal inflatable balloon. The diameter of the perforations in the proximal inflatable balloon is currently preferably from about 10 to about 150 microns, and can range typically in number from several dozen to several thousand. The distal and proximal inflatable balloons can be made of low or high compliance material, and can have a cylindrical, oval, square or rectangular shape. An interior inflation lumen 260 is provided in the blocking balloon catheter connected in fluid communication with the proximal inflatable balloon for inflation and deflation of the proximal balloon, and the catheter shaft preferably has one or more removal or evacuation ports 264 adjacent to the proximal balloon, and at least one lumen 266 connected to the proximal evacuation ports for fluid communication and emboli evacuation. The number of proximal evacuation ports typically can range from 1 to 5.

The invention also accordingly provides for a method for dissolving and removal of thrombus, stenotic or embolic material, utilizing the embolic containment system of FIG. 11, for dissolving and removal of thrombus, stenotic or embolic material. Initially, the guide wire is placed across a lesion or other desired target site within a blood vessel to be treated. The catheter bearing the blocking balloon catheter can then be threaded over the guide wire to place the distal balloon distal to the lesion and place the proximal balloon proximal to the lesion. The distal and proximal blocking balloons are then simultaneously inflated with an inflation fluid to block the portion of the blood vessel or artery being treated at both the proximal and distal balloon sites, preferably with a low fluid pressure that will not cause the inflation fluid to stream out the perforations in the balloons and/or in either of the catheters carrying the distal and proximal inflatable balloons, such as 2–3 atm. for example, to block fluid flow through the blood vessel and isolate the lesion area from surrounding vasculature.

In a seventh alternate embodiment of an emboli protection system 270, illustrated in FIG. 12, the inflatable balloons may have a balloon-in-balloon configuration, with separate lumens being provided for inside and outside balloons. Accordingly, a blocking balloon catheter 272 is provided with distal and proximal balloons, and a shaft having one or more evacuation ports of an evacuation lumen for removing emboli through the proximal end of the catheter. The blocking balloon catheter has a distal end 274 and a proximal end 276, and the shaft 278 has at least one lumen 280 for a guide wire device 282.

An outer distal inflatable balloon 284 is mounted on the shaft approximately at or near the distal end of the catheter, having a plurality of perforations 286 in the proximal face of the distal inflatable balloon facing the proximal end of catheter, and an inner non-perforated distal inflatable balloon 288 is mounted to the shaft within the outer distal inflatable balloon. An interior lumen 290 in the catheter shaft is connected in fluid communication with the outer distal balloon for inflation and deflation of the outer distal balloon, and an interior lumen 292 is provided in the catheter shaft that is connected in fluid communication with the inner distal balloon for inflation and deflation of the inner distal balloon.

Similarly, an outer proximal inflatable balloon 294 is also preferably mounted to the shaft of the blocking balloon catheter proximal to the distal inflatable balloon, and an inner non-perforated proximal inflatable balloon 298 is mounted to the catheter shaft within the outer proximal inflatable balloon. The outer proximal inflatable balloon also preferably has a plurality of perforations 296 defined in the distal surface of the proximal balloon facing away from the proximal end of the catheter. The diameter of the perforations in the outer distal and outer proximal inflatable balloons is currently preferably from about 10 to about 150 microns, and can range typically in number from several dozen to several thousand. An interior lumen 300 in the catheter shaft is connected in fluid communication with the outer proximal balloon for inflation and deflation of the outer proximal balloon, and an interior lumen 302 in the catheter shaft is connected in fluid communication with the inner proximal balloon for inflation and deflation of the inner proximal balloon. The catheter shaft also has at least one evacuation port 304 connected in fluid communication with at least one lumen 306 for evacuation of emboli from the isolated portion of the vasculature. The balloon in balloon configuration thus can permit the use of the inside balloons for inflation and blockage of flow in the portion of the blood vessel to be isolated, and the use of the outer balloons for drug delivery or flushing of emboli from the isolated portion of the blood vessel, to permit blocking and flushing to be accomplished simultaneously.

An eighth alternate embodiment of an emboli protection system 310 of the invention is illustrated in FIG. 13, in which a blocking balloon catheter 312 is provided with distal, middle, and proximal inflatable balloons mounted on the distal end of a catheter shaft. The blocking balloon catheter has a distal end 314, a proximal end 316, and a shaft 318. In a presently preferred embodiment, the shaft includes at least one lumen 320 for a guide wire device 322, over which the blocking balloon catheter can be introduced into the vasculature. A distal inflatable balloon 324 is mounted at or near the distal end of the catheter, and can be made of low or high compliance material, and can have a cylindrical, oval, square or rectangular shape, or other similar shape. An inflation lumen 325 is provided in the catheter for inflation and deflation of the distal balloon. In this embodiment, the distal balloon is non-perforated, with a plurality of fluid infusion and/or aspiration supply ports 326 provided at the distal end of catheter proximal to the distal inflatable balloon, and a fluid supply lumen 328 provided in the catheter to supply fluid to the ports 326 and to aspirate fluid from the isolated portion of the vessel to flush and evacuate emboli. An inflatable balloon 330 for expansion and placement of a stent, or a similar balloon such as an angioplasty balloon, for example, is mounted to the blocking balloon catheter, proximal to the distal inflatable balloon, with an interior lumen 332 connected in fluid communication with the angioplasty balloon for inflation and deflation of the angioplasty balloon. A proximal inflatable balloon 334 is also mounted to the catheter shaft, proximal to the angioplasty balloon, having an inflation lumen 338 for the proximal inflatable balloon. The proximal inflatable balloon can be made of low or high compliance material, and can have a cylindrical, oval, square or rectangular shape, or other similar shape.

The catheter shaft preferably also has one or more evacuation ports such as the evacuation ports 340 shown in FIG. 13 as being provided proximal to the angioplasty balloon and distal to the proximal inflatable balloon, with at least one lumen 342 being provided in the catheter shaft connected in fluid communication with the evacuation ports for emboli evacuation.

Accordingly, a method for removing emboli during angioplasty or other similar arteriovenous interventional procedures utilizing such a triple balloon emboli protection system as is described above with reference to FIG. 13 will now be described. Initially, a guide wire device is introduced into the vasculature and placed across a lesion or desired target site, and the triple balloon catheter is then introduced over the guide wire device, with the distal balloon distal to the lesion, the middle balloon at the site of the lesion, and the proximal balloon proximal to the lesion. The distal balloon can then be inflated with an inflation fluid to block the artery, and to isolate the lesion area from the surrounding vasculature. Thereafter, the middle balloon is inflated with an inflation fluid to place a stent, or to perform an angioplasty procedure, for example. The proximal balloon can then be inflated, and the middle balloon deflated to release any emboli generated by placement of the stent or angioplasty procedure. Thereafter, the middle balloon may be reinflated and deflated, such as to deploy or redeploy a stent evenly, or to a larger diameter. The proximal balloon can then be deflated, and fluid can be provided through the holes in the shaft proximal to the distal balloon for flushing emboli back through the blood vessel or artery, for removal through a proximal connector device, which can be removed for this purpose.

Referring to FIG. 14, another presently preferred alternate embodiment of an emboli protection system of the invention provides for a single balloon emboli protection system 350 for isolating a portion of a blood vessel in the vasculature, the blood vessel having a target site to be treated by an interventional device, in which a guide wire shaft is provided with an inflatable balloon mounted on the distal end of the guide wire shaft, and a one way valve in the proximal end of the shaft. The system comprises a guide wire or catheter shaft 352, having a distal end 354 and a proximal end 356, with the proximal end of the catheter shaft being connectable to a hemostatic valve 358 having a removable connector 360. An inflatable balloon 362 is mounted on or near the distal end of the guide wire or catheter shaft, and infusion ports, holes or perforations 364 are provided in the proximal face of the balloon, facing the proximal end of the guide wire shaft. At least one lumen 366 is provided in the guide wire shaft for fluid communication with the distal balloon for inflation and deflation of the balloon, and in a presently preferred embodiment, a valve 368 is provided the lumen in the proximal end of the shaft allowing for inflation and deflation of the balloon. The inflation valve is preferably operable to maintain a minimum pressure in the distal inflation balloon, permitting the balloon to remain inflated when the removable connector is removed from the hemostatic valve, so that other devices can be introduced during the procedure to be introduced over the guide wire shaft. In a presently preferred embodiment, the valve is a one way valve 368, such as a flap valve as illustrated in FIG. 14.

The infusion holes in the proximal face of the balloon are preferably dimensioned to remain sealed when the pressure of the inflation fluid is below a sufficient minimum inflation fluid pressure, in order to maintain application of a pressure to the valve which will keep the valve closed when the connector is removed. In one presently preferred embodiment, the infusion holes in the proximal face of the balloon are typically 0.001 to 0.002 inches in diameter.

Figure 15:
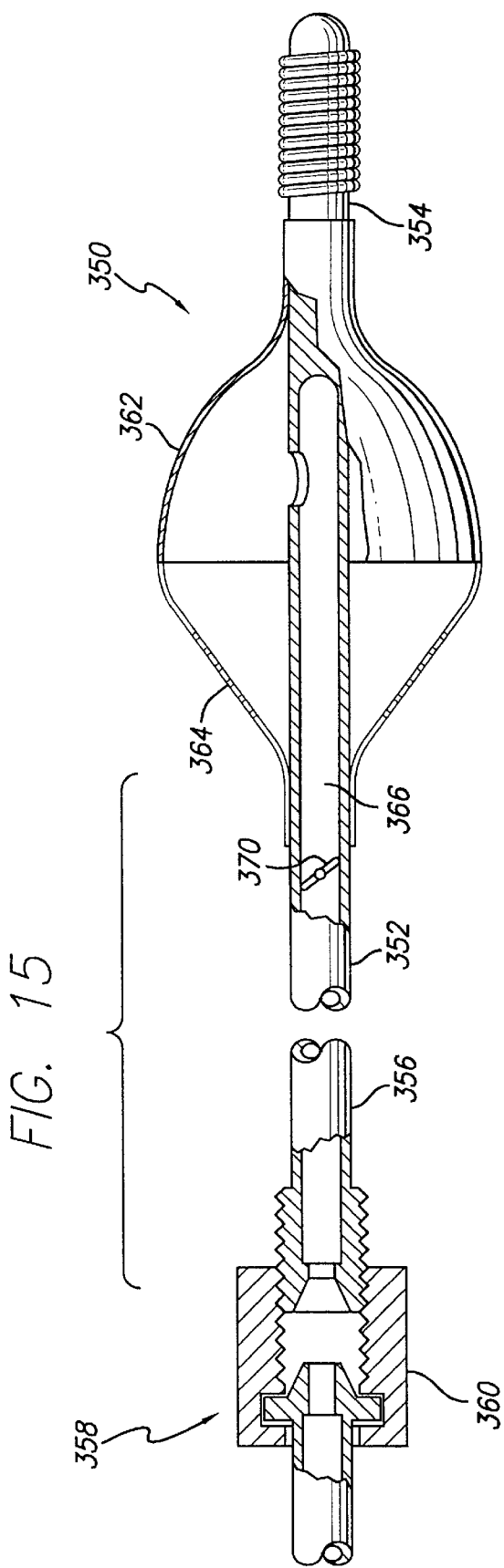
FIG. 15 is a sectional view of a tenth embodiment of an emboli protection system of the invention in which a guide wire shaft is provided with an inflatable balloon mounted on the distal end of the guide wire shaft, a lumen for fluid communication with the distal balloon, similar to that of FIG. 14, but provided with a two way valve in the proximal end of the shaft.

In one presently preferred alternate embodiment illustrated in FIG. 15, the single balloon emboli protection system is substantially identical to the embodiment of FIG. 14, but is provided with a two way valve 370 in the proximal end of the shaft, such as a butterfly valve, shown in FIG. 15.

The single balloon emboli protection system can be used in conjunction with currently compatible devices, such as balloon catheters, rapid exchange balloon catheters, stent delivery systems, guide wires, guiding catheters, angiographic catheters, and the like, and in particular can be used during vascular intervention, such as carotid artery angioplasty and stenting, in order to prevent stroke during carotid artery intervention.

According to the method of utilizing the single balloon emboli protection system for isolating a portion of a blood vessel in the vasculature, wherein the blood vessel has a target site to be treated by an interventional device, a guide wire or catheter shaft as described above is provided, and the guide wire or catheter shaft is connected to the vasculature by the removable connector. The catheter shaft is then introduced into the vasculature and across the target site in the blood vessel, and the inflatable balloon is positioned distal to the target site. Thereafter, the inflatable balloon can be inflated with an inflation fluid supplied to the inflatable balloon under a minimum pressure to block blood flow through the portion of the blood vessel, and the removable connector can then be removed from the hemostatic valve, as the inflation valve operates to maintain a minimum pressure in the distal inflation balloon enabling the balloon to remain inflated when the removable connector is removed from the hemostatic valve. While the portion of the blood vessel to be treated is thus isolated by the blocking action of the inflatable distal balloon, an interventional device is then threaded over the catheter shaft through the hemostatic valve and positioned at the target site. The interventional procedure, such as angioplasty or implantation of a stent, for example, can then be performed, and the interventional device can then be removed. Thereafter, the pressure of the inflation fluid supplied to the inflatable balloon can then be increased to cause the inflation fluid to stream out of the balloon infusion holes and to flow proximally of the inflatable balloon through the vasculature. Additional pressure can be provided to the distal inflation balloon to provide a flow of fluid through the infusion holes for providing a continuous flushing of the blood vessel proximal to the distal inflation balloon, which flows through the blood vessel, such as the external carotid artery, for example, and back through a branching of the blood vessel, such as the carotid Y branching, for example, flushing emboli to an unblocked portion of the vasculature. Following the step of increasing the pressure of the inflation fluid, the catheter shaft can be reconnected to the vasculature by the removable connector, and the inflation valve can be operated to release the pressure in the balloon to deflate the balloon, allowing the catheter shaft to be removed from the vasculature. Where the inflation valve is a one way valve, such as a flap valve, the blocking action of the valve can be overcome, such as by application of a vacuum to defeat the valve and aspirate inflation fluid from the distal balloon. Where the valve is a two way valve, such as the butterfly valve, the valve can simply be operated to open the valve to release pressure from the distal balloon.

Figure 16:
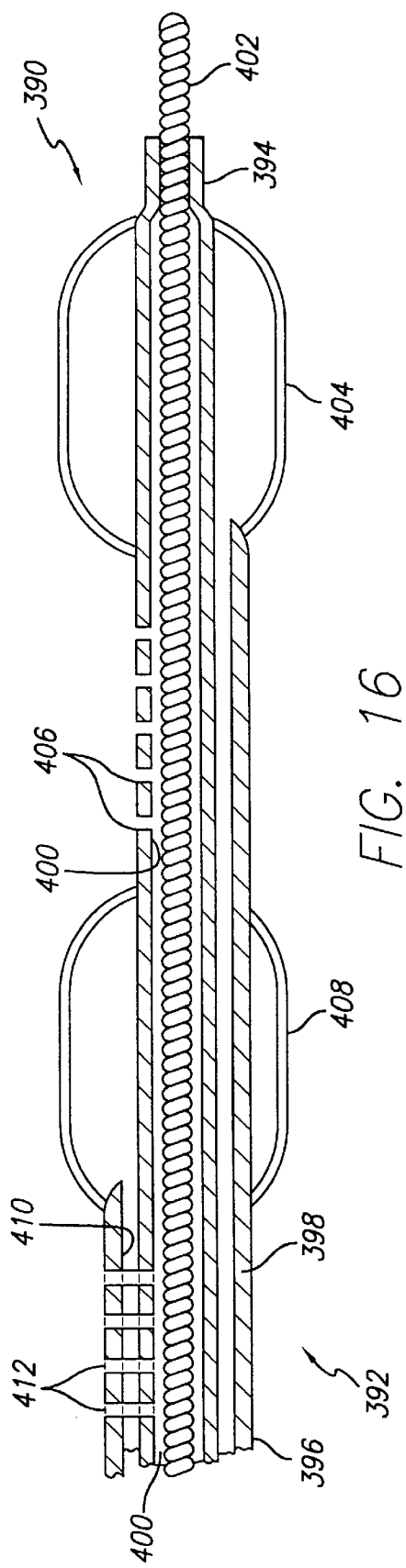
FIG. 16 is a sectional view of an eleventh embodiment showing a dual blocking balloon catheter according to the invention in which a blocking balloon catheter with distal and proximal blocking balloons includes a shaft having a retractable guide wire allowing for infusion of drugs and perfusion through the distal end of the catheter.
Figure 17:
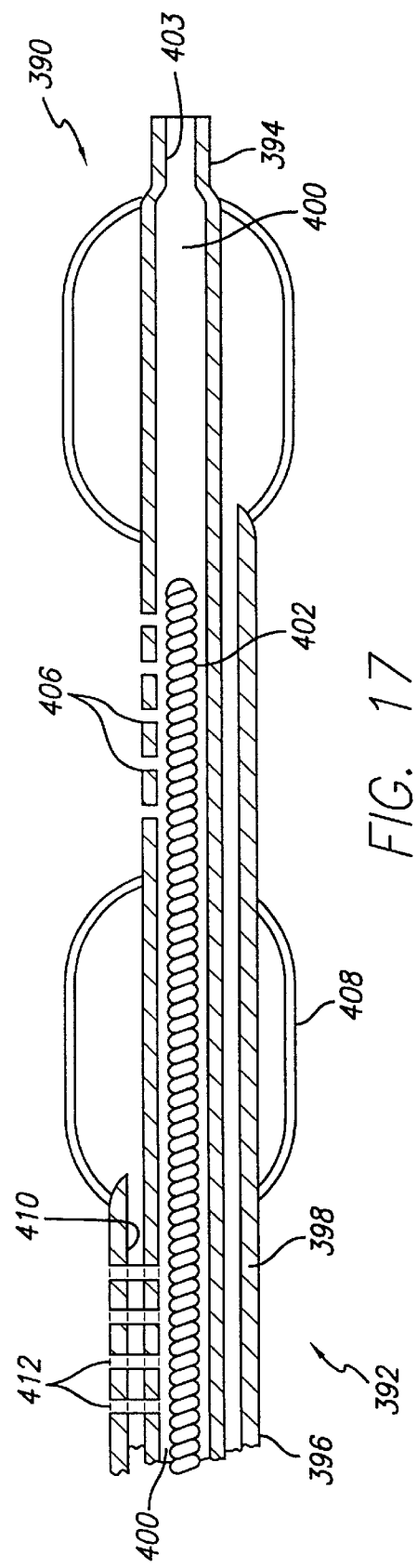
FIG. 17 is a sectional view of the dual blocking balloon catheter of FIG. 16, showing retraction of the guide wire allowing for perfusion through the distal end of the catheter.

Referring to FIGS. 16 and 17, in an eleventh embodiment, the present invention provides for an emboli protection system 390 in which a blocking balloon catheter is provided with distal and proximal balloons, and a shaft having one or more infusion ports and perfusion ports. The blocking balloon catheter 392 has a distal end 394, a proximal end 396, and a shaft 398 having a lumen 400 for a guide wire device 402. In one currently preferred embodiment, the guide wire device can be fixed to the distal end of the catheter. In an alternate preferred embodiment, as is illustrated in FIG. 17, the guide wire device can be retractable, to allow perfusion of blood flow from the distal opening 403 of the guide wire lumen 400 when the guide wire device is retracted from the distal opening of the guide wire lumen. A distal inflatable balloon 404 is mounted on the shaft approximately at or near the distal end of the catheter. A plurality of perforations or ports 406 are provided through the catheter between the proximal and distal inflatable balloons, connected in fluid communication with the guide wire lumen 400 to permit perfusion of blood or fluid to the isolated portion of the blood vessel between the proximal and distal blocking balloons.

A proximal inflatable balloon 408 is also preferably mounted to the shaft of the blocking balloon catheter proximal to the distal inflatable balloon. An interior inflation lumen 410 is provided in the blocking balloon catheter connected in fluid communication with the proximal inflatable balloon for inflation and deflation of the proximal balloon, and a plurality of perforations or ports 412 are provided through the catheter proximal to the proximal inflatable balloon, connected in fluid communication with the guide wire lumen 400, to permit perfusion of blood between the area of the blood vessel proximal to the proximal balloon to the area of the blood vessel distal to the distal balloon through the distal opening 403 when the guide wire is retracted, as is shown in FIG. 17.

Figure 18:
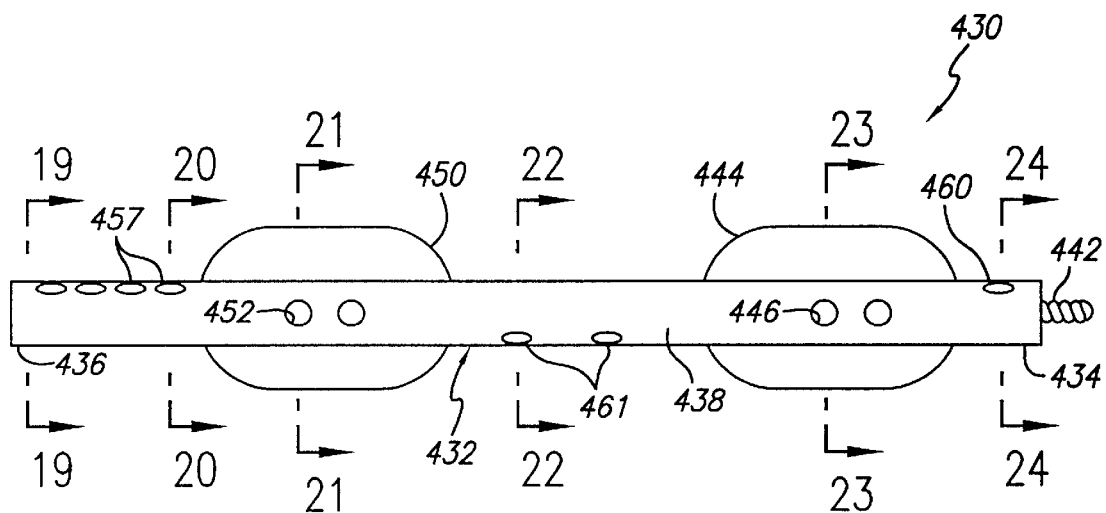
FIG. 18 is a schematic diagram of a twelfth embodiment showing a dual blocking balloon catheter according to the invention having distal and proximal blocking balloons and a shaft with a fixed guide wire and multiple lumens and ports allowing for infusion of drugs and perfusion through the catheter.
Figure 19:
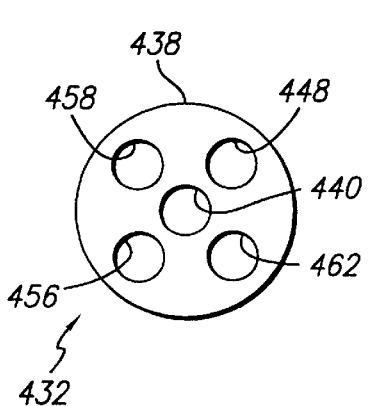
FIG. 19 is a sectional view of the dual blocking balloon catheter taken along line 19—19 of FIG. 18.
Figure 20:
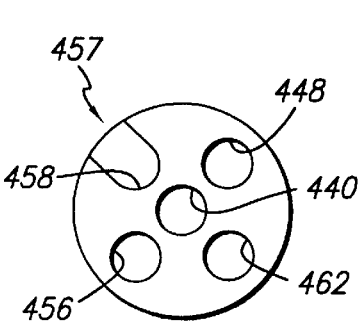
FIG. 20 is a sectional view of the dual blocking balloon catheter taken along line 20—20 of FIG. 18.
Figure 21:
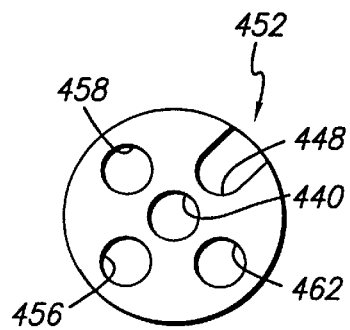
FIG. 21 is a sectional view of the dual blocking balloon catheter taken along line 21—21 of FIG. 18.
Figure 22:
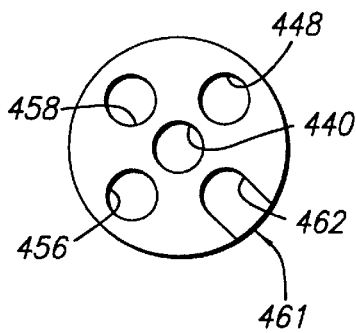
FIG. 22 is a sectional view of the dual blocking balloon catheter taken along line 22—22 of FIG. 18.
Figure 23:
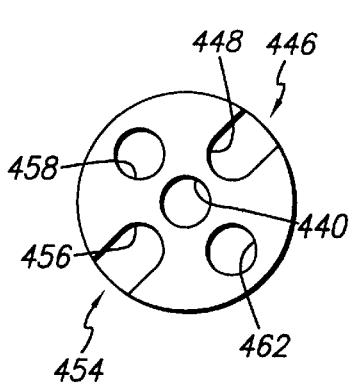
FIG. 23 is a sectional view of the dual blocking balloon catheter taken along line 23—23 of FIG. 18.

As is illustrated in FIGS. 18 to 24, in a twelfth embodiment, the present invention provides for an emboli protection system 430 in which a blocking balloon catheter is provided with distal and proximal balloons, and a shaft having multiple infusion ports and perfusion ports which may be drilled through the catheter to connect with corresponding lumens within the catheter. Although the lumens are depicted herein as being circular, the lumens may also be "D" shaped, oval, elliptical, or any other similar shape, and may be formed as a multi-lumen extrusion, from a series of fused extrusions fused together, or from multiple tubes fused together, or a combination thereof. The blocking balloon catheter 432 has a distal end 434, a proximal end 436, and a shaft 438 having a lumen 440, illustrated in FIGS. 19 to 24, for a guide wire device 442. Referring to FIGS. 18 and 23, a distal inflatable balloon 444 is mounted on the shaft approximately at or near the distal end of the catheter, and the distal inflatable balloon is connected in fluid communication through distal inflation ports 446 through the balloon inflation lumen 448 for inflation and deflation of the distal inflatable balloon. Referring to FIGS. 18 and 21, a proximal inflatable balloon 450 is preferably mounted to the shaft of the blocking balloon catheter proximal to the distal inflatable balloon, and the proximal inflatable balloon is connected in fluid communication through proximal inflation ports 452 through the balloon lumen 448 for inflation and deflation of the proximal inflatable balloon. Alternatively, as is shown in FIG. 23, the distal inflatable balloon may optionally be inflatable separately from the proximal inflatable balloon, by provision of alternate distal inflation ports 454 through a dedicated distal inflatable balloon inflation lumen 456 for inflation and deflation of the distal inflatable balloon.

Figure 24:
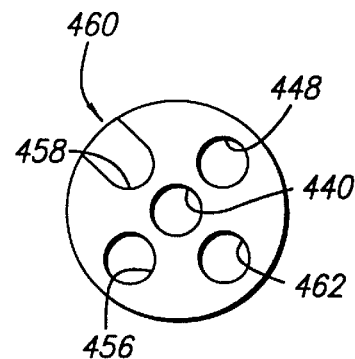
FIG. 24 is a sectional view of the dual blocking balloon catheter taken along line 24—24 of FIG. 18.

The catheter shaft is also provided with multiple infusion and perfusion lumens, to allow infusion of therapeutic drugs or fluid, and to allow passive perfusion of blood flow from the blood vessel being treated between the area of the blood vessel proximal to the proximal balloon to the area of the blood vessel distal to the distal balloon. The catheter shaft can be formed as an extrusion having multiple lumens, or as multiple extrusions of lumens fused together, or a combination of both. Referring to FIGS. 18, 20 and 24, a plurality of perforations or ports 457 are provided through the catheter proximal to the proximal inflatable balloon, connected in fluid communication with the perfusion lumen 458, and one or more perforations or ports 460 are provided through the catheter distal to the distal inflatable balloon, connected in fluid communication with the perfusion lumen 458, to permit perfusion of blood between the area of the blood vessel proximal to the proximal balloon to the area of the blood vessel distal to the distal balloon. Referring to FIGS. 18 and 22, a plurality of perforations or ports 461 are provided through the catheter between the distal and proximal inflatable balloons, connected in fluid communication with an infusion lumen 462 extending to the proximal end of the catheter to permit infusion of a therapeutic drug or fluid to the isolated portion of the blood vessel being treated.

Figure 25:
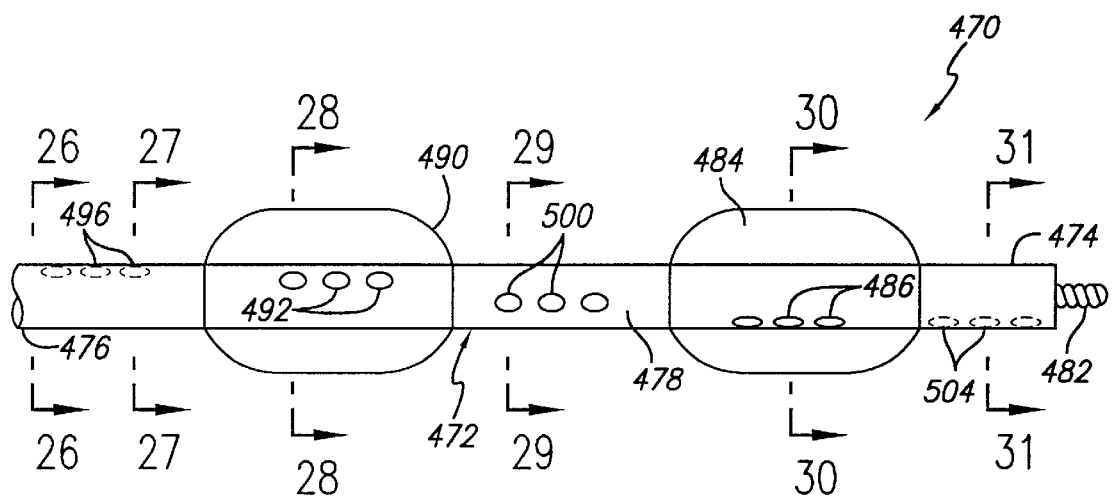
FIG. 25 is a schematic diagram of a thirteenth embodiment showing a dual blocking balloon catheter according to the invention having distal and proximal blocking balloons and a shaft with a fixed guide wire and multiple lumens and ports allowing for infusion of drugs and perfusion through the catheter.
Figure 26:
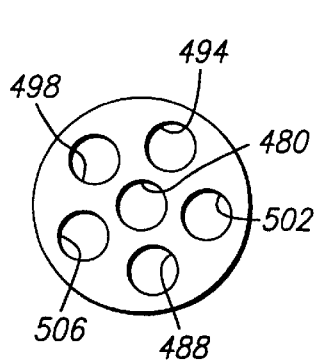
FIG. 26 is a sectional view of the dual blocking balloon catheter taken along line 26—26 of FIG. 25.
Figure 27:
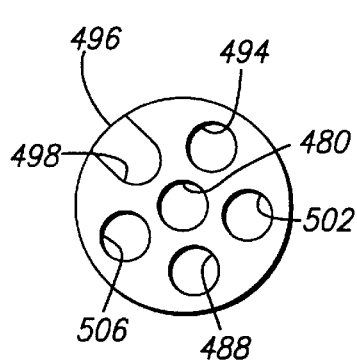
FIG. 27 is a sectional view of the dual blocking balloon catheter taken along line 27—27 of FIG. 25.
Figure 28:
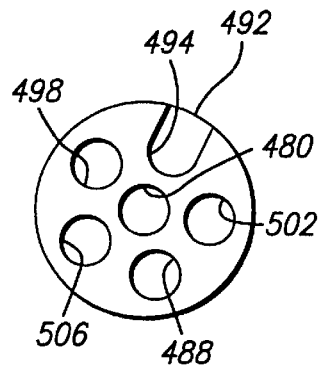
FIG. 28 is a sectional view of the dual blocking balloon catheter taken along line 28—28 of FIG. 25.
Figure 29:
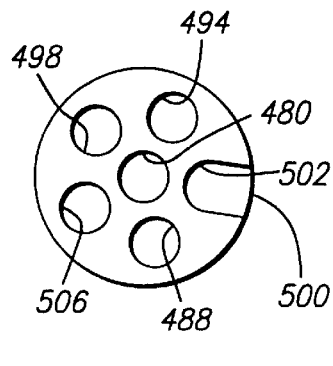
FIG. 29 is a sectional view of the dual blocking balloon catheter taken along line 29—29 of FIG. 25.
Figure 30:
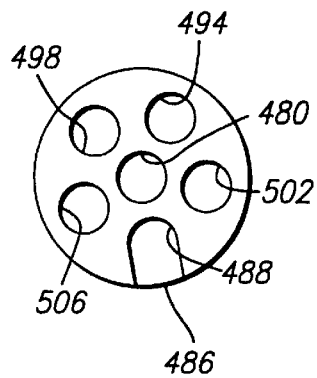
FIG. 30 is a sectional view of the dual blocking balloon catheter taken along line 30—30 of FIG. 25.

As is illustrated in FIGS. 25 to 31, in a thirteenth embodiment, the present invention provides for an emboli protection system 470 in which a blocking balloon catheter is provided with distal and proximal balloons, and a shaft having multiple infusion ports which may be drilled through the catheter to connect with corresponding lumens within the catheter. Although the lumens are depicted herein as being circular, the lumens may also be "D" shaped, oval, elliptical, or any other similar shape, and may be formed as a multi-lumen extrusion, from a series of fused extrusions fused together, or from multiple tubes fused together, or a combination thereof. The blocking balloon catheter 472 has a distal end 474, a proximal end 476, and a shaft 478 having a lumen 480, illustrated in FIGS. 26 to 31, for a guide wire device 482. Referring to FIGS. 25 and 30, a distal inflatable balloon 484 is mounted on the shaft approximately at or near the distal end of the catheter, and the distal inflatable balloon is connected in fluid communication through distal inflation ports 486 through the distal balloon inflation lumen 488 for inflation and deflation of the distal inflatable balloon. Referring to FIGS. 25 and 28, a proximal inflatable balloon 490 is preferably mounted to the shaft of the blocking balloon catheter proximal to the distal inflatable balloon, and the proximal inflatable balloon is connected in fluid communication through proximal inflation ports 492 through the proximal balloon lumen 494 for inflation and deflation of the proximal inflatable balloon, independently of inflation and deflation of the distal balloon.

Figure 31:
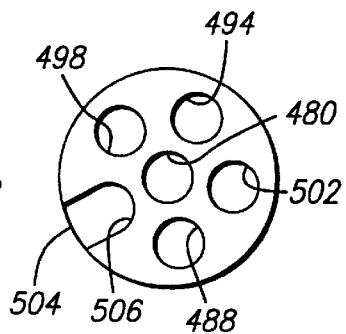
FIG. 31 is a sectional view of the dual blocking balloon catheter taken along line 31—31 of FIG. 25.

The catheter shaft is provided with multiple infusion lumens, to allow infusion of therapeutic drugs or fluid to the area of the blood vessel being treated. Referring to FIGS. 25, 27 and 31, a plurality of perforations or ports 496 are provided through the catheter proximal to the proximal inflatable balloon, connected in fluid communication with the infusion lumen 498, to permit infusion of therapeutic drugs or fluid to the area of the blood vessel being treated. Similarly, a plurality of perforations or ports 500 are provided through the catheter between the proximal and distal inflatable balloons, connected in fluid communication with the infusion lumen 502 to permit infusion of therapeutic drugs or fluid to the isolated portion of the blood vessel being treated, and a plurality of perforations or ports 504 are provided through the catheter distal to the distal inflatable balloon, connected in fluid communication with the infusion lumen 506, to permit infusion of therapeutic drugs or fluid to the area of the blood vessel being treated.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An emboli protection system for isolating a portion of a blood vessel having a target site to be treated by an interventional procedure to prevent migration of emboli into the rest of the vasculature, comprising:

a distal blocking balloon catheter having distal and proximal ends, said distal blocking balloon catheter having a shaft with an inflatable balloon mounted on the shaft near the distal end of the catheter, the shaft having at least one lumen for a guide wire and at least one lumen for fluid communication with the inflatable balloon, and the inflatable balloon of the distal blocking balloon catheter having a surface defining a plurality of perforations facing the proximal end of the catheter;

a proximal blocking balloon catheter adapted to be introduced in the vasculature over said distal blocking balloon catheter, said proximal blocking balloon catheter having distal and proximal ends, said proximal blocking balloon catheter having a shaft with an inflatable balloon mounted on the shaft near the distal end of the catheter, the shaft having at least one lumen for a guide wire and at least one lumen for fluid communication with the inflatable balloon, and the inflatable balloon of the proximal blocking balloon catheter having a surface defining a plurality of perforations facing away from the proximal end of the proximal blocking balloon catheter, the shaft of said proximal blocking balloon catheter including at least one exit port and a lumen connected to said exit port for fluid communication with the interior lumen of the isolated portion of the blood vessel; and an inflation fluid supply connected in fluid communication with said inflatable balloons of said distal and proximal blocking balloon catheters for supplying inflation fluid to said inflatable balloons under pressure, whereby said inflation fluid exits the perforations and flushes emboli in the isolated portion of the blood vessel through the exit port of the proximal blocking balloon catheter and proximally through the fluid communication lumen of the proximal blocking balloon catheter.

2. The emboli protection system of claim 1, wherein said exit port comprises an annular opening at the distal end of said shaft of said proximal blocking balloon catheter.

3. The emboli protection system of claim 1, further comprising an interventional therapeutic device adapted to be introduced into the vasculature over said distal blocking balloon catheter and to be disposed between said distal blocking balloon catheter and said proximal blocking balloon catheter.

4. The emboli protection system of claim 3, wherein said interventional therapeutic device comprises an angioplasty balloon catheter.

5. The emboli protection system of claim 1, wherein said distal blocking balloon catheter comprises an interventional therapeutic device mounted on said shaft of said distal blocking balloon catheter.

6. The emboli protection system of claim 5, wherein said interventional therapeutic device comprises an angioplasty balloon catheter.

7. The emboli protection system of claim 1, wherein said inflation fluid comprises a thrombolytic inflation fluid, in order to break down and dissolve any thrombus and plaque in the isolated portion of the blood vessel through both a chemical effect of the thrombolytic inflation fluid, and flow of the thrombolytic inflation fluid in the isolated portion of the blood vessel.

8. An emboli protection system for isolating a portion of a blood vessel to be treated by an interventional procedure to prevent migration of emboli into the rest of the vasculature, comprising:
   a blocking balloon catheter having distal and proximal ends, said blocking balloon catheter having a shaft with a distal inflatable balloon mounted on the shaft near the distal end of the catheter, the shaft having at least one lumen for a guide wire and at least one lumen for fluid communication with the inflatable balloon, and the inflatable balloon of the blocking balloon catheter having a surface defining a plurality of perforations facing the proximal end of the catheter;
   an interventional therapeutic device mounted on said shaft of said blocking balloon catheter proximal to said distal inflatable balloon;
   a proximal inflatable balloon mounted on the shaft proximal to said interventional device, and the proximal inflatable balloon having a surface defining a plurality of perforations facing away from the proximal end of the blocking balloon catheter, the shaft of said blocking balloon catheter including at least one exit port and a lumen connected to said exit port for fluid communication with the interior lumen of the isolated portion of the blood vessel; and
   an inflation fluid supply connected in fluid communication with said distal and proximal inflatable balloons for supplying inflation fluid to said inflatable balloons under pressure, whereby said inflation fluid exits the perforations and flushes emboli in the isolated portion of the blood vessel through the exit port of the shaft of the blocking balloon catheter and proximally through the fluid communication lumen connected to the exit port.

9. The emboli protection system of claim 8, wherein said interventional therapeutic device comprises an angioplasty balloon catheter.

10. The emboli protection system of claim 8, wherein said inflation fluid comprises a thrombolytic inflation fluid, in order to break down and dissolve any thrombus and plaque in the isolated portion of the blood vessel through both a chemical effect of the thrombolytic inflation fluid, and flow of the thrombolytic inflation fluid in the isolated portion of the blood vessel.

11. A method for removing emboli during arteriovenous interventional procedures for treatment of a target site of a portion of a blood vessel in the vasculature, comprising the steps of:
   providing a distal blocking balloon catheter having a shaft and a distal inflatable balloon mounted thereon, the distal inflatable balloon having a surface defining a plurality of perforations facing the proximal end of the catheter, and a proximal blocking balloon catheter adapted to be disposed over said distal blocking balloon catheter, said proximal blocking catheter having a shaft and a proximal inflatable balloon mounted thereon, the proximal inflatable balloon having a surface defining a plurality of perforations facing away from the proximal end of the proximal blocking balloon catheter, and said proximal blocking catheter having an exit port and a lumen connected to said exit port for fluid communication with the interior lumen of the portion of the blood vessel;
   placing a guide wire across a target site in the blood vessel in the vasculature;
   threading the distal blocking balloon catheter over the guide wire and positioning the distal inflatable balloon distal to the target site;
   providing an interventional device for performing an interventional procedure at the target site;
   threading said interventional device over the shaft of the distal blocking balloon catheter and positioning said interventional device at the target site;
   threading the proximal blocking balloon catheter over the interventional device and positioning the proximal inflatable balloon proximal to the target site;
   initially inflating the distal and proximal inflatable balloons simultaneously with an inflation fluid to block blood flow through the portion of the blood vessel to isolate the target site area from surrounding vasculature;
   inflating the distal and proximal inflatable balloons to cause the inflation fluid to stream out of the balloon perforations, whereby fluid supplied to the inflatable balloons of the distal and proximal blocking balloon catheters exits the perforations and flushes emboli in the isolated portion of the blood vessel through the exit port of the proximal blocking balloon catheter and proximally through the fluid communication lumen of the proximal blocking balloon catheter;
   performing the interventional procedure;
   removing the interventional device; and
   increasing fluid pressure inside the proximal and distal inflatable balloons to increase flow and pressure within the blocked section and remove emboli from the blocked section through the exit port of the proximal blocking balloon catheter.

12. The method of claim 11, wherein said step of initially inflating the distal and proximal inflatable balloons comprises inflating said distal and proximal inflatable balloons with a pressure in the range of about 2 to 3 atm.

13. The method of claim 12, further comprising the step of varying the pressure of inflation fluid supplied to the proximal and distal inflation balloons.

14. The method of claim 13, wherein said step of varying the pressure of inflation fluid supplied to the proximal and distal inflation balloons comprises alternately increasing the pressure of inflation fluid supplied to the proximal inflation balloon while decreasing the pressure of inflation fluid supplied to the distal inflation balloon, and decreasing the pressure of inflation fluid supplied to the proximal inflation balloon while increasing the pressure of inflation fluid supplied to the distal inflation balloon, to cause corresponding changes in the flow direction of the inflation fluid into the interior lumen of the isolated portion of the blood vessel, and to create additional turbulence in order to flush out any remaining emboli.

15. The method of claim 11, wherein said interventional procedure is angioplasty.

16. The method of claim 11, wherein said inflation fluid is a thrombolytic inflation fluid that is connected in fluid communication with the inflatable balloons of the distal and proximal blocking catheters, and the thrombolytic inflation fluid is used to inflate the distal and proximal blocking balloons simultaneously with the thrombolytic inflation fluid to block the artery at both balloon sites, and to cause the thrombolytic fluid to stream out of the balloon perforations and flow through the central lumen of the proximal blocking catheter and out of the patient's body, in order to break down and dissolve any thrombus and plaque in the isolated portion of the blood vessel through both the chemical effect of the drug and the streaming or jetting action of the fluid.

17. An emboli protection system for isolating a portion of a blood vessel having a target site to be treated by an interventional procedure to prevent migration of emboli into the rest of the vasculature, and for removal of thrombus, stenotic or embolic material, comprising:

a blocking balloon catheter having distal and proximal ends, said blocking balloon catheter having a shaft with a distal inflatable balloon mounted to the catheter shaft near the distal end of the catheter, and a proximal inflatable balloon mounted to the catheter shaft, the shaft having at least one lumen for a guide wire and at least one lumen for fluid communication with the distal and proximal inflatable balloons, the shaft having a surface defining at least one evacuation port between the distal and proximal balloons and an evacuation lumen connected in fluid communication with said at least one evacuation port for removing emboli through the proximal end of the catheter, and at least one of the distal and proximal inflatable balloons having a surface defining a plurality of perforations facing toward said at least one evacuation port; and an inflation fluid supply connected in fluid communication with said distal and proximal inflatable balloons for supplying inflation fluid under pressure to said inflatable balloons under pressure for inflating said distal and proximal balloons in the blood vessel on either side of the target site to be treated, thereby isolating the portion of the blood vessel, and whereby said inflation fluid exits said perforations and flushes emboli in the isolated portion of the blood vessel through the evacuation port of the blocking balloon catheter and proximally through the evacuation lumen of the blocking balloon catheter.

18. The emboli protection system of claim 17, wherein said distal inflatable balloon has a surface defining a plurality of perforations facing the proximal end of the catheter, and said proximal inflatable balloon has a surface defining a plurality of perforations facing away from the proximal end of the catheter.

19. The emboli protection system of claim 17, wherein said distal inflatable balloon has a balloon-in-balloon configuration, with said distal inflatable balloon comprising a first inflatable balloon mounted to the catheter shaft near the distal end of the catheter, and a second inflatable balloon being disposed within said first inflatable balloon and mounted to the catheter shaft, said first inflatable balloon connected in fluid communication with said at least one lumen communicating with said distal and proximal inflatable balloons, said first inflatable balloon having a surface defining a plurality of perforations facing the proximal end of the catheter, and said second inflatable balloon being connected in fluid communication through a lumen in said catheter shaft with said inflation fluid supply, to permit supply of said inflation fluid to said first and second inflatable balloons independently.

20. The emboli protection system of claim 17, wherein said proximal inflatable balloon has a balloon-in-balloon configuration, with said proximal inflatable balloon comprising a first inflatable balloon mounted to the catheter shaft proximal to said distal inflatable balloon, and a second inflatable balloon being disposed within said first inflatable balloon and mounted to the catheter shaft, said first inflatable balloon connected in fluid communication with said at least one lumen communicating with said distal and proximal inflatable balloons, said first inflatable balloon having a surface defining a plurality of perforations facing away from the proximal end of the catheter, and said second inflatable balloon being connected in fluid communication through a lumen in said catheter shaft with said inflation fluid supply, to permit supply of said inflation fluid to said first and second inflatable balloons independently.

21. The emboli protection system of claim 17, wherein said inflation fluid supply comprises a supply of thrombolytic inflation fluid, in order to break down and dissolve any thrombus and plaque in the isolated portion of the blood vessel through both a chemical effect of the thrombolytic inflation fluid, and flow of the thrombolytic inflation fluid in the isolated portion of the blood vessel.

22. An emboli protection system for isolating a portion of a blood vessel having a target site to be treated by an interventional procedure and for dissolving and removal of thrombus, stenotic or embolic material, comprising:

a blocking balloon catheter having distal and proximal ends, said blocking balloon catheter having a shaft with a distal inflatable balloon mounted to the catheter shaft near the distal end of the catheter, and a proximal inflatable balloon mounted to the catheter shaft, the shaft having at least one lumen for a guide wire and at least one lumen for fluid communication with the distal and proximal inflatable balloons, the shaft having a surface defining at least one evacuation port between the distal and proximal balloons and an evacuation lumen connected in fluid communication with said at least one evacuation port for removing emboli through the proximal end of the catheter, said distal inflatable balloon having a surface defining a plurality of perforations facing the proximal end of the catheter, and said proximal inflatable balloon having a surface defining a plurality of perforations facing away from the proximal end of the catheter; and a thrombolytic inflation fluid supply connected in fluid communication with said distal and proximal inflatable balloons for supplying inflation fluid under pressure to said inflatable balloons under pressure for inflating said distal and proximal balloons in the blood vessel on either side of the target site to be treated, thereby isolating the portion of the blood vessel, and whereby said inflation fluid exits said perforations and flushes emboli in the isolated portion of the blood vessel through the evacuation port of the blocking balloon catheter and proximally through the evacuation lumen of the blocking balloon catheter, and to thereby break down and dissolve any thrombus and plaque in the isolated portion of the blood vessel through both a chemical effect of the thrombolytic inflation fluid, and flow of the thrombolytic inflation fluid in the isolated portion of the blood vessel.

23. The emboli protection system of claim 22, wherein said distal inflatable balloon has a balloon-in-balloon configuration, with said distal inflatable balloon comprising a first inflatable balloon mounted to the catheter shaft near the distal end of the catheter, and a second inflatable balloon being disposed within said first inflatable balloon and mounted to the catheter shaft, said first inflatable balloon connected in fluid communication with said at least one lumen communicating with said distal and proximal inflatable balloons, said first inflatable balloon having a surface defining a plurality of perforations facing the proximal end of the catheter, and said second inflatable balloon being connected in fluid communication through a lumen in said catheter shaft with said inflation fluid supply, to permit supply of said inflation fluid to said first and second inflatable balloons independently.

24. The emboli protection system of claim 22, wherein said proximal inflatable balloon has a balloon-in-balloon configuration, with said proximal inflatable balloon comprising a first inflatable balloon mounted to the catheter shaft proximal to said distal inflatable balloon, and a second inflatable balloon being disposed within said first inflatable balloon and mounted to the catheter shaft, said first inflatable balloon connected in fluid communication with said at least one lumen communicating with said distal and proximal inflatable balloons, said first inflatable balloon having a surface defining a plurality of perforations facing away from the proximal end of the catheter, and said second inflatable balloon being connected in fluid communication through a lumen in said catheter shaft with said inflation fluid supply, to permit supply of said inflation fluid to said first and second inflatable balloons independently.

25. A method for isolating a portion of a blood vessel having a target site to be treated by an interventional procedure and for dissolving and removal of thrombus, stenotic or embolic material, comprising the steps of:
providing an embolic containment system for dissolving and removal of thrombus, stenotic or embolic material having a blocking balloon catheter with a shaft having at least one evacuation port, a distal inflatable balloon and a proximal inflatable balloon for isolating the portion of the blood vessel, at least one of the distal and proximal inflatable balloons having a surface defining a plurality of perforations facing toward said at least one evacuation port;
placing a guide wire across a target site in the vasculature to be treated;
threading the blocking balloon catheter over the guide wire to place the distal balloon distal to the target site and place the proximal balloon proximal to the target site; and
inflating the distal and proximal blocking balloons simultaneously with a thrombolytic inflation fluid to block the artery at both balloon sites, to thereby isolate the lesion area from surrounding vasculature, and to cause the thrombolytic fluid to stream out of the balloon perforations.

26. An emboli protection system for isolating a portion of a blood vessel in the vasculature, the blood vessel having a target site to be treated by an interventional device, comprising:
a catheter shaft having distal and proximal ends, said proximal end of said catheter shaft being connectable to the vasculature by a hemostatic valve having a removable connector, said catheter shaft having an inflatable balloon mounted on the distal end of the catheter shaft, said inflatable balloon having a surface defining a plurality of perforations in the balloon facing the proximal end of the shaft, and said shaft having at least one lumen for fluid communication with the distal balloon;
an inflation valve disposed in the said catheter shaft allowing for inflation and deflation of the balloon, and said inflation valve being operable to maintain a minimum pressure in the distal inflation balloon enabling said balloon to remain inflated when the removable connector is removed from the hemostatic valve and allowing introduction of the interventional device into the vasculature and to the target site in the blood vessel to be treated over said catheter shaft.

27. The emboli protection system of claim 26, wherein said inflation valve is disposed in the proximal end of said catheter shaft.

28. The emboli protection system of claim 26, wherein said catheter shaft comprises a guide wire.

29. The emboli protection system of claim 26, wherein said plurality of perforations are dimensioned to remain sealed until a minimum inflation fluid pressure is applied to said inflation balloon, in order to apply the minimum pressure to the inflation valve to keep the inflation valve closed when the removable connector is removed.

30. The emboli protection system of claim 26, wherein said perforations are approximately from 0.001 to 0.002 inches in diameter.

31. A method for isolating a portion of a blood vessel in the vasculature, the blood vessel having a target site to be treated by an interventional device, comprising the steps of:
providing a catheter shaft having a proximal end connectable to the vasculature by a hemostatic valve having a removable connector, said catheter shaft having an inflatable balloon mounted on the distal end of the catheter shaft, said inflatable balloon having a surface defining a plurality of perforations in the balloon facing the proximal end of the shaft, said shaft having at least one lumen for fluid communication with the distal balloon, and an inflation valve disposed in the said catheter shaft allowing for inflation and deflation of the balloon;
connecting the catheter shaft to the vasculature by the removable connector;
introducing the catheter shaft into the vasculature and across the target site in the blood vessel and positioning the inflatable balloon distal to the target site;
inflating the inflatable balloon with an inflation fluid supplied to the inflatable balloon under a minimum pressure to block blood flow through the portion of the blood vessel;
removing the removable connector from the hemostatic valve, said inflation valve operating to maintain a minimum pressure in the distal inflation balloon enabling said balloon to remain inflated when the removable connector is removed from the hemostatic valve;
threading an interventional device over the catheter shaft through the hemostatic valve and positioning the interventional device at the target site; and
increasing the pressure of the inflation fluid supplied to the inflatable balloon to cause the inflation fluid to stream out of the balloon perforations and to flow proximally of said inflatable balloon through the vasculature.

32. The method of claim 31, further comprising the steps of:
prior to the step of increasing the pressure of the inflation fluid, performing the interventional procedure; and
removing the interventional device.

33. The method of claim 31, further comprising the steps of:
following said step of increasing the pressure of the inflation fluid, reconnecting the catheter shaft to the vasculature by the removable connector;
operating said inflation valve to deflate said balloon; and
removing said catheter shaft from the vasculature.

34. A method for removing emboli during an arteriovenous interventional procedure for treatment of a target site in a blood vessel, comprising the steps of:
providing a triple balloon emboli protection system having a catheter shaft with a distal inflatable balloon, a proximal inflatable balloon, and a middle inflatable balloon having a stent mounted thereon;
placing the catheter shaft across the target site with the distal inflatable balloon distal to the target site, the middle inflatable balloon at the target site, and the proximal inflatable balloon proximal to the target site;
inflating the distal inflatable balloon with an inflation fluid to block the blood vessel in order to isolate the target site from surrounding vasculature;
inflating the middle inflatable balloon with an inflation fluid to place the stent at the target site;
inflating the proximal inflatable balloon;
deflating the middle inflatable balloon to release any emboli generated by placement of the stent; and
reinflating the middle inflatable balloon and deflating the middle inflatable balloon to deploy the stent evenly.

35. The method of claim 34, wherein said catheter shaft has a surface defining at least one fluid evacuation port and at least one fluid infusion port proximal to distal balloon, said at least one fluid evacuation port being in fluid communication with a fluid evacuation lumen in said catheter shaft, and said at least one fluid infusion port being in fluid communication with a fluid infusion lumen provided in said catheter shaft for supplying fluid through the fluid infusion port to flush emboli through said evacuation lumen, and further comprising the steps of:
deflating the proximal inflatable balloon and providing fluid through said at least one fluid infusion port in the catheter shaft proximal to the distal balloon for flushing emboli back through the blood vessel for removal through a proximal connector device.

36. A method for removing emboli during an arteriovenous interventional procedure for treatment of a target site in a blood vessel, comprising the steps of:
providing a triple balloon emboli protection system having a catheter shaft with a distal inflatable balloon, a proximal inflatable balloon, and a middle inflatable balloon having a stent mounted thereon;
placing the catheter shaft across the target site with the distal inflatable balloon distal to the target site, the middle inflatable balloon at the target site, and the proximal inflatable balloon proximal to the target site;
inflating the distal inflatable balloon with an inflation fluid to block the blood vessel in order to isolate the target site from surrounding vasculature;
inflating the middle inflatable balloon with an inflation fluid to place the stent at the target site;
inflating the proximal inflatable balloon;
deflating the middle inflatable balloon to release any emboli generated by placement of the stent; and
reinflating the middle inflatable balloon and deflating the middle inflatable balloon to deploy the stent to a larger diameter.

37. The method of claim 36, wherein said catheter shaft has a surface defining at least one fluid evacuation port and at least one fluid infusion port proximal to distal balloon, said at least one fluid evacuation port being in fluid communication with a fluid evacuation lumen in said catheter shaft, and said at least one fluid infusion port being in fluid communication with a fluid infusion lumen provided in said catheter shaft for supplying fluid through the fluid infusion port to flush emboli through said evacuation lumen, and further comprising the steps of:
deflating the proximal inflatable balloon and providing fluid through said at least one fluid infusion port in the catheter shaft proximal to the distal balloon for flushing emboli back through the blood vessel for removal through a proximal connector device.

38. An emboli protection system for isolating a portion of a blood vessel having a target site to be treated by an interventional procedure to prevent migration of emboli into the rest of the vasculature, comprising:
a blocking balloon catheter having distal and proximal ends, said blocking balloon catheter having a shaft with a distal inflatable balloon mounted to the catheter shaft near the distal end of the catheter, and a proximal inflatable balloon mounted to the catheter shaft, the shaft having at least one guide wire lumen and at least one lumen for fluid communication with the distal and proximal inflatable balloons, the shaft having a surface defining at least one port through the shaft proximal to the proximal balloon and at least one port between the proximal and distal inflatable balloons, each said port connected in fluid communication with said guide wire lumen to permit perfusion of blood to the isolated portion of the blood vessel through each said port between said proximal and distal blocking balloons, and
an inflation fluid supply connected in fluid communication with said distal and proximal inflatable balloons for supplying inflation fluid under pressure to said inflatable balloons under pressure for inflating said distal and proximal balloons in the blood vessel on either side of the target site to be treated, thereby isolating the portion of the blood vessel.

39. The emboli protection system of claim 38, wherein said guide wire lumen includes a distal opening, and further comprising a retractable guide wire device disposed within said guide wire lumen, whereby said guide wire is retracted from distal opening to permit perfusion of blood between the area of the blood vessel proximal to the proximal balloon to the area of the blood vessel distal to the distal balloon through said distal opening when the guide wire is retracted.

* * * * *